(12) United States Patent
Basser et al.

(10) Patent No.: US 10,871,539 B2
(45) Date of Patent: Dec. 22, 2020

(54) DETERMINATION OF A JOINT PROBABILITY DISTRIBUTION OF RADIUS AND LENGTH OF ANISOTROPIC PORES FROM DOUBLE PULSED FIELD GRADIENT MRI DATA

(71) Applicant: The United States of America, as represented by the Secretary, Department of Health and Human Services, Bethesda, MD (US)

(72) Inventors: Peter J. Basser, Washington, DC (US); Dan H. Benjamini, Rockville, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 803 days.

(21) Appl. No.: 15/529,412

(22) PCT Filed: Nov. 24, 2015

(86) PCT No.: PCT/US2015/062489
§ 371 (c)(1),
(2) Date: May 24, 2017

(87) PCT Pub. No.: WO2016/086025
PCT Pub. Date: Jun. 2, 2016

(65) Prior Publication Data
US 2018/0335496 A1  Nov. 22, 2018

Related U.S. Application Data

(60) Provisional application No. 62/083,834, filed on Nov. 24, 2014.

(51) Int. Cl.
*G01R 33/567* (2006.01)
*G01R 33/563* (2006.01)
*G16H 10/40* (2018.01)

(52) U.S. Cl.
CPC ..... *G01R 33/567* (2013.01); *G01R 33/56341* (2013.01); *G16H 10/40* (2018.01)

(58) Field of Classification Search
CPC . G01R 33/567; G01R 33/56341; G16H 10/40
See application file for complete search history.

(56) References Cited

U.S. PATENT DOCUMENTS 5,539,310 A * 7/1996 Basser ............. G01R 33/56341
324/307
7,643,863 B2   1/2010 Basser et al.
(Continued)

OTHER PUBLICATIONS

Bernstein, D., et al. "An Experimental Approach to the Evaluation of the Biopersistence of Respirable Synthetic Fibers and Minerals," Environmental Health Perspectives. 102(5), 1994. p. 15-18 (Year: 1994).*

(Continued)

*Primary Examiner* — Keith M Raymond
*Assistant Examiner* — Sean A Frith
(74) *Attorney, Agent, or Firm* — Klarquist Sparkman, LLP

(57) ABSTRACT

Described herein are exemplary methods for estimating a nonparametric joint radius-length (R-L) distribution of an ensemble of porous elements represented generally by finite cylinders. Some described methods comprise estimating an eccentricity distribution of a group of anisotropic porous elements. For example, disclosed methods can be applied to estimate a nonparametric joint R-L distribution of injured axons in nervous tissue, muscle tissue, plant elements, or other porous materials. Employing a novel three dimensional (3-D) double pulsed-field gradient (d-PFG) magnetic (Continued)

resonance (MR) acquisition scheme, both the marginal radius and length distributions of a population of generally cylindrical porous elements can be obtained. The marginal radius and length distributions can then b e used to constrain and stabilize the estimate of the joint radius-length distribution. Using the marginal distributions as constraints allows the joint R-L distribution to be reconstructed from an underdetermined system (i.e., more variables than equations).

19 Claims, 13 Drawing Sheets

(56) References Cited

U.S. PATENT DOCUMENTS

| 7,711,171 | B2 | 5/2010 | Basser et al. | |
|---|---|---|---|---|
| 2008/0051665 | A1* | 2/2008 | Xu | A61B 5/0059 600/476 |
| 2009/0280493 | A1* | 11/2009 | Wirtz | C12Q 1/6886 435/6.11 |
| 2010/0033182 | A1* | 2/2010 | Ozarslan | G01R 33/44 324/309 |
| 2012/0259199 | A1* | 10/2012 | Huwer | G01R 33/56341 600/410 |
| 2014/0184220 | A1 | 7/2014 | Paulsen et al. | |
| 2014/0184224 | A1* | 7/2014 | Nevo | G06T 7/0012 324/318 |

OTHER PUBLICATIONS

Yano et al "Math, Numerics, & Programming for Mechanical Engineers," 2.086 Numerical Computation for Mechanical Engineers. 2012. p. 1-198 (Year: 2012).*

Ozarslan, E., "Compartment Shape Anisotropy (CSA) Revealed by Double Pulsed Field Gradient MR," Journal Magnetic Resonance, 199(1). 2009. p. 56-67 (Year: 2009).*

Yost, G.P. "Lectures on Probability and Statistics," Imperial College Statistics Course, 1983. (Year: 1983).*

Qiao, Y. et al. "Diffusion Correlation NMR Spectroscopic Study of Anisotropic Diffusion of Water in Plant Tissues," Biophysical Journal vol. 89, 2005. p. 2899-2905 (Year: 2005).*

Liu, A., et al. "Traumatic Brain Injury: Diffusion-Weighted MR Imaging Findings," Am J Neuroradiology. vol. 20, 1999. p. 1636-1641 (Year: 1999).*

Benjamini et al., "Estimation of pore size distribution using concentric double pulsed-field gradient NMR," *Journal of Magnetic Resonance*, 230:198-204 (Mar. 14, 2013).

Benjamini et al., "Joint radius-length distribution as a measure of anisotropic pore eccentricity: An experimental and analytical framework," *The Journal of Chemical Physics*, 141:214202-214212 (Oct. 14, 2014).

Benjamini et al., "MRI Measurement of Three-Dimensional Morphological Features of Axons," Proceedings of the International Society for Magnetic Resonance in Medicine, 23rd Annual Meeting and Exhibition, Toronto, CA, May 30-Jun. 5, 2015.

Benjamini et al., "Pore size distribution of bioresorbable films using a 3-D diffusion NMR method," *Acta Biomaterialia*, 10:2762-2768 (Feb. 15, 2014).

Benjamini et al., "White matter microstructure from nonparametric axon diameter distribution mapping," *NeuroImage* 135:333-44 (2016).

International Search Report and Written Opinion for related International Application No. PCT/US2015/062489, dated Mar. 8, 2016, 15 pages.

Lawrenz et al., "A tensor model and measures of microscopic anisotropy for double-wave-vector diffusion-weighting experiments with long mixing times," *Journal of Magnetic Resonance*, 202:43-56 (Jan. 1, 2010).

Lawrenz et al., "Simultaneous Estimation of Compartment Size and Eccentricity with Double-Wave-Vector Tensor Imaging at Long Mixing Times," Proceedings of the International Society for Magnetic Resonance in Medicine, 20th Annual Meeting and Exhibition, Melbourne, Australia, May 5-11, 2012.

Shemesh et al., "Mapping apparent eccentricity and residual ensemble anisotropy in the gray matter using angular double-pulsed-field-gradient MRI," *Magnetic Resonance in Medicine*, 68:794-806 (Nov. 29, 2011).

* cited by examiner

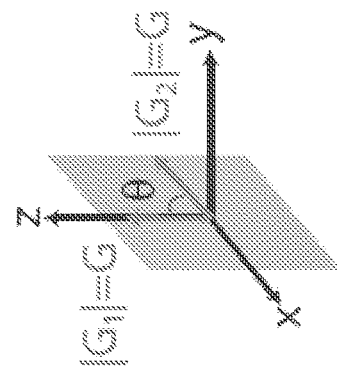 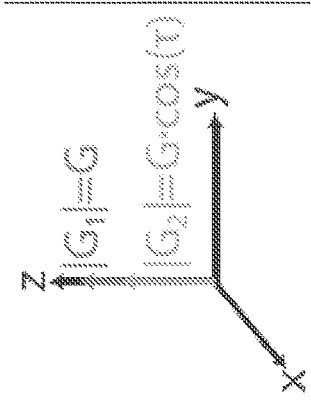 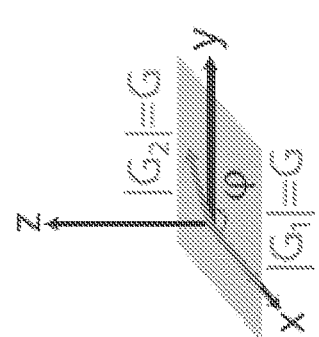 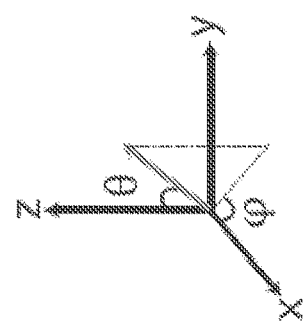
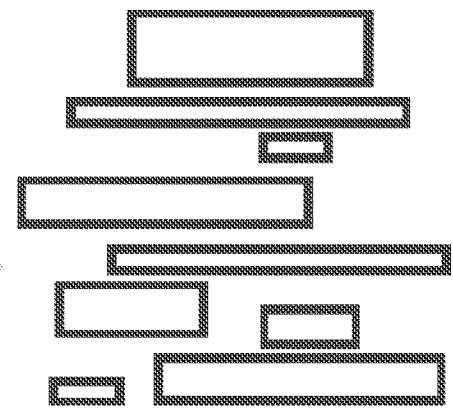 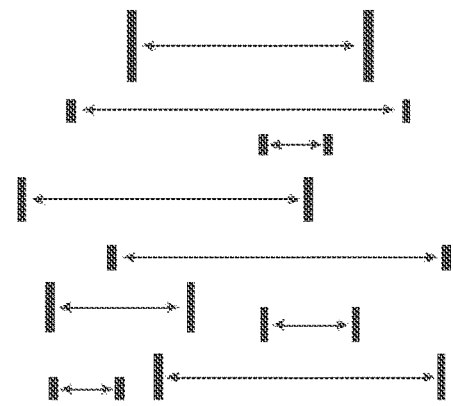 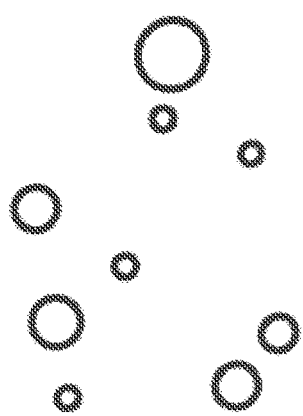 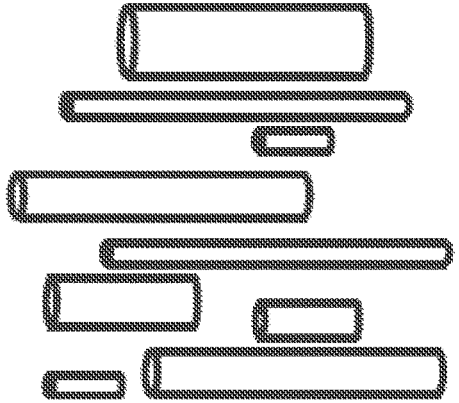
FIG. 1A  FIG. 1B  FIG. 1C  FIG. 1D

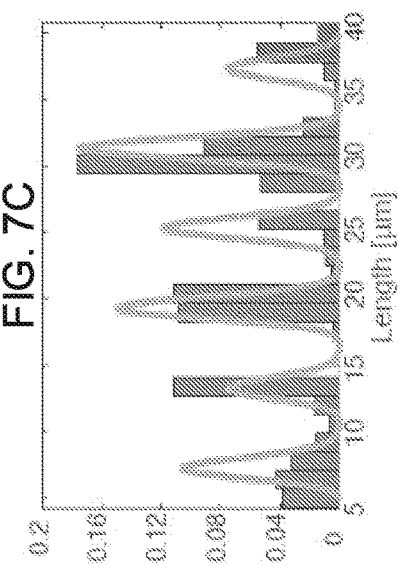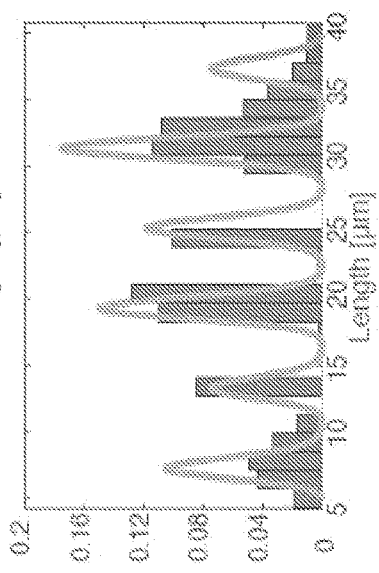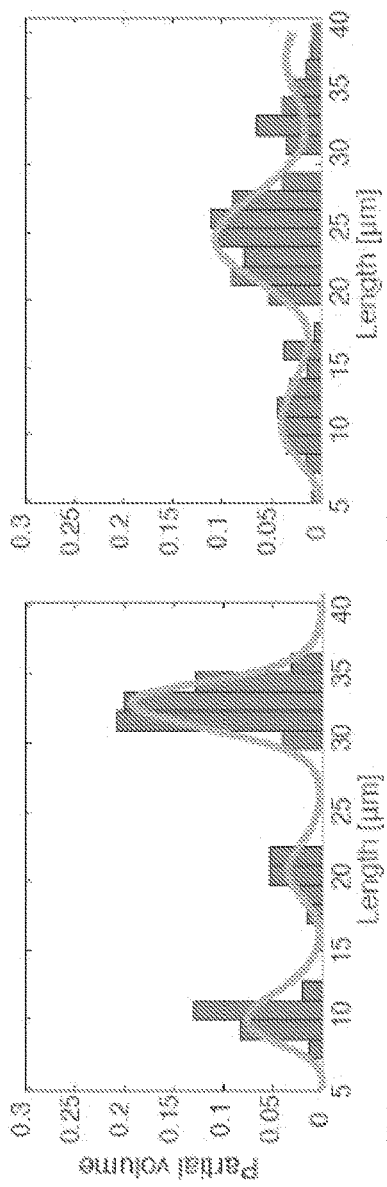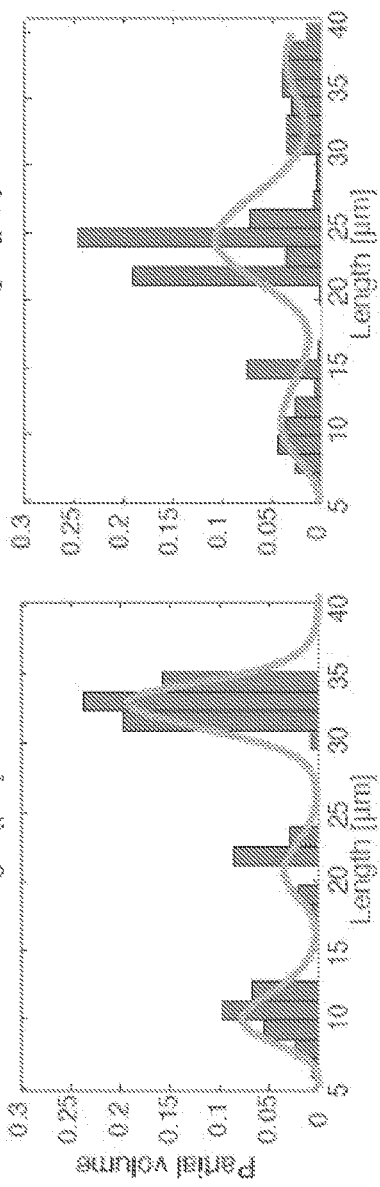
FIG. 7A  FIG. 7B  FIG. 7C  FIG. 7D  FIG. 7E  FIG. 7F

DETERMINATION OF A JOINT PROBABILITY DISTRIBUTION OF RADIUS AND LENGTH OF ANISOTROPIC PORES FROM DOUBLE PULSED FIELD GRADIENT MRI DATA

CROSS-REFERENCE TO RELATED APPLICATIONS

This application is the U.S. National Stage of International Application No. PCT/US2015/062489, filed Nov. 24, 2015, which claims the benefit of U.S. Provisional Application No. 62/083,834 filed Nov. 24, 2014, which is incorporated by reference herein.

FIELD

This application is related to estimating the shape and size distribution of elements in a porous media using diffusion magnetic resonance techniques.

SUMMARY

Described herein are exemplary methods for estimating, or determining, a nonparametric joint radius-length (R-L) distribution of an ensemble of porous elements represented generally by finite cylinders. Some described methods comprise estimating, or determining, an eccentricity distribution of a group of anisotropic porous elements. For example, disclosed methods can be applied to estimate a nonparametric joint R-L distribution of injured axons in nervous tissue. Employing a novel three dimensional (3-D) double pulsed-field gradient (d-PFG) magnetic resonance (MR) acquisition scheme, both the marginal radius and length distributions of a population of generally cylindrical porous elements can be obtained. The marginal radius and length distributions can then be used to constrain and stabilize the estimate of the joint radius-length distribution. Using these marginal distributions as constraints allows the joint R-L distribution to be reconstructed from an underdetermined system (i.e., more variables than equations), which requires a relatively small and feasible number of MR acquisitions.

To demonstrate the process, two simulated representative joint R-L distribution phantoms corrupted by different noise levels were reconstructed using this new framework. As expected, the broader the peaks in the joint distribution, the less stable and more sensitive to noise the estimation of the marginal distributions. Nevertheless, the reconstruction of the joint distribution is remarkably robust to increases in noise level or decreases in the signal-to-noise (SNR); this characteristic can be attributed to the use of the marginal distributions as constraints. Axons exhibit local compartment eccentricity variations upon injury, and the extent of these variations depends on the severity of the injury. Nonparametric estimation of the eccentricity distribution of injured axonal tissue is of particular interest since generally one cannot assume a parametric distribution a priori. Reconstructing the eccentricity distribution can provide vital information about changes resulting from injury.

The foregoing and other objects, features, and advantages of the disclosed technology will become more apparent from the following detailed description, which proceeds with reference to the accompanying figures.

BRIEF DESCRIPTION OF THE DRAWINGS

FIGS. 1A-1D are illustrations of an exemplary experimental framework. (1A) A 3-D schematic drawing of an ensemble of capped cylinders (bottom), aligned with the z-axis of a spherical coordinate system (top). (1B) In an x-y plane experiment the polar angle, $\theta$, is $\pi/2$, while $\phi$ is varied along with the direction of G2 (top), resulting in structural information from the cross section of the cylinder (bottom). (1C) in a z-axis experiment the amplitude of G2 varies according to $|G2|=G \cos(\tau)$, while all other parameters are kept constant (top), resulting in structural information from the parallel direction of the cylinder (bottom). (1D) A cross section of the x-z plane, where both the radius and the length play a role (bottom). Here, G2 changes its direction according to $\theta$, while $\phi=\pi/2$ (top).

FIGS. 6A-6F and FIGS. 7A-7F are the theoretical (solid line) and estimated (bins) MRDs of all of the phantoms. Dense-narrow distribution with noise standard deviations of (A) 0.5% and (D) 1%. Scattered-broad distribution with noise standard deviations of (B) 0.5% and (E) 1%. Random-diagonal distribution with noise standard deviations of (C) 0.5% and (F) 1%.

DETAILED DESCRIPTION

I. Introduction

Figure 2:
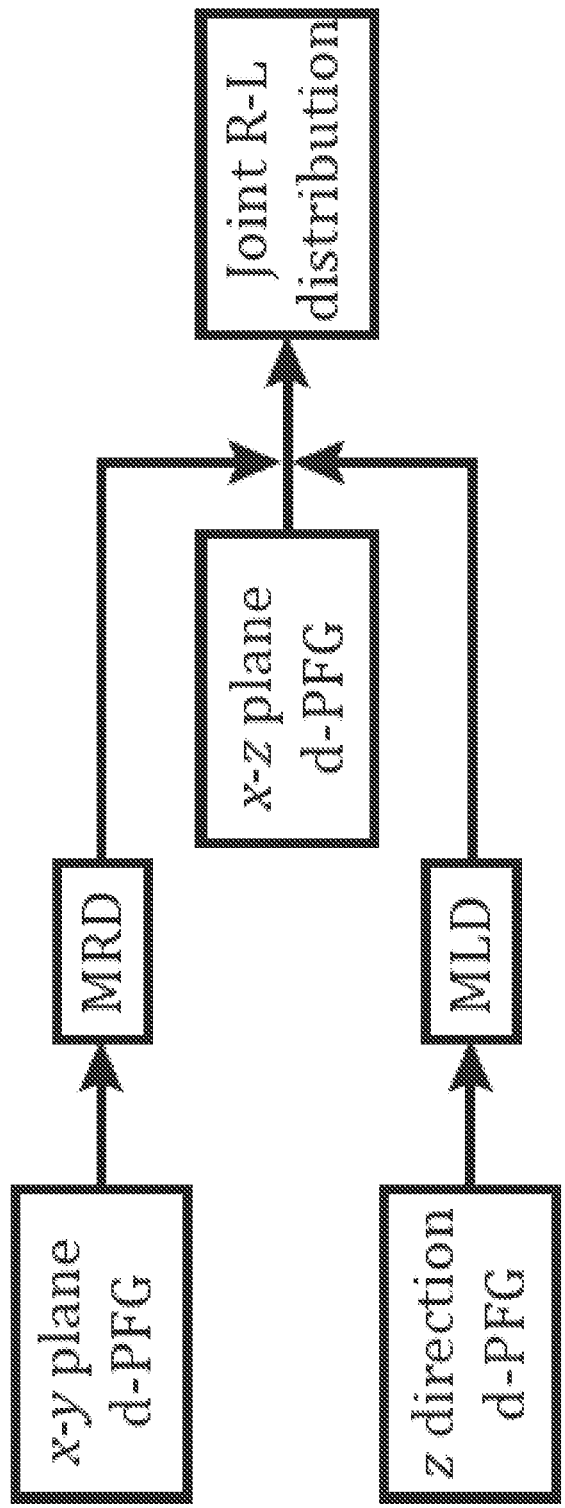
FIG. 2 is a block diagram of the experimental and analytical framework. The marginal radius and length distributions, respectively, MRD and MLD, are used to estimate the joint R-L distribution.

The shape and size distribution of pores strongly influence transport processes in and material properties of porous media. As used herein, the term "pores" means any porous elements that exhibit substantially greater diffusion along a first direction (e.g., an axial or length direction) relative to diffusion in directions perpendicular to the first direction (e.g., radial directions). For example, the morphological features of pore shape and pore size can affect the macroscopic electrical conductivity, thermal conductivity, hydraulic permeability, solute and solvent diffusivity, as well as the mechanical stiffness, susceptibility to fracture, and many other properties. Pores that are not spherical and largely aligned with one another can result in macroscopic tensorial relationships between generalized flows or fluxes and forces.

In biology, shape and pore-size distribution strongly influence macroscopic functional properties. In the nervous system, axons can be viewed as being impermeable cylindrical pores whose diameter is known to be correlated with the conduction velocity of nervous impulses. In addition, the distribution of diameters of these axons, and thus the distribution of velocities of nerve impulses, is a determinant of the amount of information that can propagate along a bundle of axonal fibers or fascicles. Furthermore, quantification of the compartment shape eccentricity, in addition to its size, is particularly valuable in injured axons, as it is known to change following mechanical, chemical, or metabolic insults.

This local variation in pore-shape eccentricity is usually referred to as "beaded" axonal morphology, and its noninvasive characterization is of great value in assessing the functional status of nervous tissue. In muscle, another fibrous tissue, the individual components that comprise the muscle fiber are long tubular cells (myocytes). Their length and cross-sectional area are proportional to the muscle functional properties, such as the relationship between muscle force and shortening velocity. Cortical bone is another biological porous material, which contains anisotropic anatomic pores (trabeculae) of different sizes. These anatomic microstructural variations have a significant impact on the material properties of cortical bone and are also known to be affected by age and disease. Finally, in plant biology, the sieve tubes, which are part of the phloem tissue that conducts nutrients, can be viewed as elongated cylindrical cells that are connected at their ends and separated by porous plates. These sieve tube elements are critical in regulating water and nutrient flow, but a quantitative characterization of their structure and morphology is still lacking. The disclosed technology provides such information.

MR provides many types of contrasts that can be used to determine features of pore microstructure and morphology. For instance, diffusion MR of spin-labeled mobile molecules within pores permits the inference of features of pore shape and size from their net displacement distribution and its dependence on diffusion time. The single pulsed-field gradient (s-PFG) MR method is commonly used to obtain this size and shape information. This method consists of a single pair of magnetic field gradient pulses of duration $\delta$, with a separation $\Delta$ embedded within a conventional Hahn spin-echo MR experiment. The restricting nature of pores can result in estimates of average pore size or macroscopic anisotropy.

The compartment shape anisotropy (CSA) of capped cylinders can be measured using a variant of the s-PFG MR method, the double-PFG (d-PFG) MR method. In d-PFG MR, two PFG pairs with amplitudes $G_1$ and $G_2$, and a prescribed relative angle between them, are applied successively, separated by a mixing time, $\tau_m$. The d-PFG method is sensitized to the temporal correlations of molecular motion within the two diffusion periods and is sensitive to the direction of the applied gradients. Using the d-PFG method, one can obtain the average pore size and the microscopic anisotropy. As the relative angle is varied, 3-D information regarding the restricting compartment can be obtained, including the CSA. In the case of a capped cylinder geometry, knowing the radius and length can provide an exact estimate of eccentricity.

In many cases, the MR signal is generated from an ensemble of polydisperse pores. Estimating the pore size distribution (PSD) can be performed using an assumed parametric distribution. This quantity can also be estimated empirically, without a priori information (i.e., non-parametrically) using s-PFG nuclear magnetic resonance (NMR) in conjunction with solving a system of linear equations. The stability and accuracy of the solution depend on the degree of linear independence of the columns of the transfer matrix (the matrix that describes the set of linear equations), which effectively measures the correlation between the independent variables. The solution to this inverse problem of estimating the PSD becomes more ill-posed as the degree of linear dependence and condition number increase. To stabilize PSD estimation, a d-PFG rather than a s-PFG MR experiment can be used. Using a d-PFD method adds an independent second dimension to the parameter space that acts to constrain the estimates of pore shape and size. Exemplary benefits of d-PFG in the context of PSD estimation are discussed and demonstrated herein, along with considerations for optimal experimental design, and validated on calibrated cylindrical microcapillary MR phantoms, resulting in accurate PSI) estimation. Such methods are described with application to drug-releasing bioresorbable porous polymer films, resulting in the estimate of a continuous size distribution of spherical pores.

PSD estimation can be readily obtained from pores assumed to be either infinite cylinders or spheres, both having an isotropic compartment shape. However, to derive a PSD of an ensemble of anisotropic pores, the system can be described by at least a bivariate size distribution instead of a single or univariate distribution. A finite (capped) cylinder, for instance, can be characterized by a 2-D joint size distribution function (R-L distribution), consequently having a marginal radius distribution (MRD) and a marginal length distribution (MLD). The term "radius" is broadly used to describe cross-sectional dimensions of circular cross-sections, ovals, ellipses, or other irregular annular shapes. With a circle, a single exact radius defines the shape. However, with an ellipse, the "radius" can be defined as a function of the major and minor axis dimensions, such as the geometric mean of the two dimensions. The "radius" of other non-circular annular cross-sections can also be defined as the effective radius that defines a circle having the same cross-sectional area as the subject non-circular cross-section (e.g., the effective radius can equal the square root of the cross-sectional area divided by $\pi$).

Described herein is a framework to estimate the joint R-L distribution of a population of capped cylinders by encoding specific planes of the specimen using d-PFG MR. This unique design allows for separate derivation of the complex spatial information from the parallel and the perpendicular dimensions of the cylinder and then use of this information to reconstruct the joint R-L distribution. Two simulated representative joint distribution phantoms corrupted by different noise levels were then used to reconstruct the ground-truth joint R-L distribution, II. Theory Isotropic shapes have been considered using a model that describes their nonparametric PSD. In such cases, it has been assumed that the acquired signal is the superposition of the calculated signals originating from the different isotropic pores. The signal can be expressed as $$E^{data}(\Omega_k) = \sum_i \Psi(R_i) E(\Omega_k, R_i), \qquad (1)$$

where $\Psi(R_i)$ are the volumetric fractions, or the PSD, which satisfy $\Sigma_i \Psi(R_i)=1$. $\Omega_k$ is the $k^{th}$ experimental parameter set, i.e., a combination of G, $\delta$, $\Delta$, and the gradient direction, which in a spherical coordinate system is given by the polar and azimuthal angles, $\theta$ and $\phi$ (FIG. 1A). In this example, the 3-D parameter space that is formed solely by varying $\Delta$, G and $\phi/\theta$ is considered. Higher dimensional information (e.g., $\Delta_1 \neq \Delta_2$ or variation of $\delta$) can be easily incorporated into this framework. A parameter, $\tau$, is introduced according to which the amplitude of $G_2$ is varied in a z-axis experiment (FIG. 1C). This example is comprehensively discussed in the Marginal length distribution subsection. Different $\Omega$s are used to transform Eq. 1 to a linear set of equations, which can be written as the matrix equation data $$E^{data}(\Omega) = E(\Omega, R)\Psi(R), \qquad (2)$$

where $E^{data}(\Omega)$ is the experimental data vector, $\Psi(R)$ is the vector of relative volumetric fractions of each pore size, and $E(\Omega, R)$ is the transfer matrix. $\Psi(R)$ is estimated by a non-negative least-square algorithm with an added constraint, that $\Sigma_i \Psi(R_i)=1$, or $$\min(\|E^{data}(\Omega) - E(\Omega, R)\Psi(R)\|^2) \qquad (3)$$

subject to $$\sum_i \Psi(R_i) = 1, \Psi(R_i) \geq 0. \qquad (4)$$

When an ensemble of capped cylinders with distributions of radii, R, and lengths, L, is considered, the most comprehensive feature embodying this microstructural information is their joint R-L distribution matrix, $\Psi(R, L)$. Owing to the separation of position variables in both the parallel and perpendicular directions of the capped cylinder, we suggest that the directionality of the diffusion encoding can be used in the same manner to obtain a complete microstructural description.

If Eq. 1 is applied in a straightforward manner to obtain the joint distribution, $\Psi(R, L)$ is written as a vector that includes the relative volumetric fractions of all the possible R and L combinations. In such a case the large number of coefficients that would need to be estimated (i.e., number of columns of the transfer matrix) would require an even larger number of acquisitions, leading to an unstable solution and an infeasible experimental period of time with which to acquire this MR data.

Instead, we suggest applying the concept of separation of variables in an experimental way by a two-step experiment, first independently finding the marginal radius and length distributions and then estimating their joint distribution. The first step involves performing a set of d-PFG experiments with gradients encoding the orthogonal perpendicular and parallel directions of the cylinder. Both marginal radius and length distributions can be estimated only if the diffusion encoding occurs exclusively in the perpendicular and parallel directions, respectively. Then, to estimate the joint distribution, a d-PFG experiment set with gradients encoding the x-z plane is performed, thus correlating displacements along the two orthogonal axes. The marginal radius and length distributions are then used as equality constraints for the estimation of the joint distribution. This pipeline is depicted schematically in FIG. 2.

A. Marginal Radius Distribution

The use of gradients that encode the x-y plane by varying the azimuthal angle, $\phi$, between the two PFG pairs, enables the MRD to be estimated, while avoiding molecular displacement information from the parallel direction (FIG. 1B). Therefore, in this case, the length of the capped cylinder does not affect the signal attenuation, and the 3-D transfer matrix, $E^{xy}(\Omega, R, L)$, is naturally reduced to a two-dimensional matrix, since L is degenerate:

$$E^{xy}(\Omega, R, L) = E^{xy}(\Omega, R), \qquad (5)$$

and Eq. 1 becomes $$E^{data}(\Omega_k) = \sum_i \Psi(R_i) E^{xy}(\Omega_k, R_i), \qquad (6)$$

$\Psi(R)$ can then be estimated from $$E^{data}(\Omega) = E^{xy}(\Omega, R)\Psi(R). \qquad (7)$$

by solving Eq. 3.

B. Marginal Length Distribution

In the case of the MLD, to avoid any x-y component in the acquired signal, the relative angle between the PEG pairs cannot be varied and both pairs have to point along the z direction. Using an s-PEG experiment in the z-direction might be possible but would lead to only one experimental variable, G. The disadvantages of using a 1-D acquisition in the context of pore size distribution estimation were previously studied and discussed. In addition to the extended information resulting from a 2-D acquisition, the s-PFG experiment has a lower number of maximal acquired data points, since the minimal step size of G is limited by hardware. Instead, we suggest a novel d-PFG acquisition with both PFG pairs applied over the parallel direction, where $|G_1|=G$ and $|G_2|=G \cos(\tau)$; this acquisition would lead to two experimental variables, G and $\tau$, as shown in FIG. 1C. The values for $|G_2|$ were chosen according to a cosine since it is the projection of the parallel (to the cylinder's symmetry axis) component of an arbitrary gradient on the x-z plane.

When this sequence is used, the radius of the capped cylinder does not affect the signal attenuation, and the 3-D transfer matrix, $E^{zz}(\Omega, R, L)$, is naturally reduced to a two-dimensional matrix, since R is degenerate:

$$E^{zz}(\Omega, R, L) = E^{zz}(\Omega, L), \qquad (8)$$

and Eq. 1 becomes $$E^{data}(\Omega_k) = \sum_i \Psi(L_i) E^{zz}(\Omega_k, L_i). \qquad (9)$$

$\Psi(L)$ can then be estimated from $$E^{data}(\Omega) = E^{zz}(\Omega, L)\Psi(L), \qquad (10)$$

by solving Eq. 3.

C. The Joint Radius-Length Distribution

Before continuing with the strategy to obtain the joint. R-L distribution, it is important to recognize the two possible cases in a bivariate distribution. The cylinder radius and length can be either statistically independent or dependent. If R and L are statistically independent random variables, their joint probability can be expressed as $$\Psi(R,L) = \Psi(R)\Psi(L)^T, \quad (11)$$

and since both marginal probabilities have been already found, estimating $\Psi(R, L)$ becomes trivial using Eq. 11, But for the general case, R and L may be correlated. To obtain this information about correlations of pore dimensions along the two orthogonal axes, parallel and perpendicular, we suggest using a d-PFG experiment with gradient directions that vary in the x-z plane, as shown in FIG. 1D. Since in each measurement both the perpendicular and parallel axes of the capped cylinder are being encoded, we can no longer ignore one of the cylinder's dimensions. It follows that the transfer matrix is indeed 3-D. Furthermore, the probability density function now depends on both R and L, and is in fact the joint distribution, $\Psi(R, L)$. In this case Eq. 1 can be written as:

$$E^{xz}(\Omega_k) = \sum_i \sum_j \Psi(R_i, L_j) E^{xz}(\Omega_k, R_i, L_j), \quad (12)$$

where $$\Sigma_i \Sigma_j \Psi(R_i, L_j) = 1.$$

As suggested earlier, to solve Eq. 12, the matrix $\Psi(R, L)$ is written as a vector. Instead of the two variables, R and L, we shall define $\Lambda = (R, L)$, which is a combination of a specific R-L couples. Therefore a system of N radii and M lengths should have N·M (R, L) couples, $\Lambda$. Eq. 12 is then reduced to $$E^{xz}(\Omega_k) = \sum_p \Psi(\Lambda_p) E^{xz}(\Omega_k, \Lambda_p), \quad (13)$$

where $$\Sigma_p \Psi(\Lambda_p) = 1.$$

Because the number of coefficients that must be estimated here is N·M, which is normally, large, the large amount of acquired data required for this measurement soon becomes infeasible. Adding equality constraints to Eq. 3 stabilizes the inversion by limiting and narrowing the solution space of the least-square minimization. This vital process can be achieved since we have obtained the two marginal distributions, $\Psi(R)$ and $\Psi(L)$, already which are related to the joint distribution as $$\sum_j \Psi(R_i, L_j) = \Psi(R) \text{ and } \sum_i \Psi(R_i, L) = \Psi(L). \quad (14)$$

Applying the equality constraints in Eq. 14 while solving the minimization problem in Eq. 3, leads to a stable nonparametric estimation of the joint radius-length distribution. Because of these constraints, the system can be underdetermined (i.e., more variables than equations) and yet be solvable.

The current framework allows a direct measurement of the anisotropy variation within the sample in the form of cylinder eccentricity distribution. Using Ozarslan's definition of the finite cylinder's eccentricity, $E=L/(2R)$, the eccentricity probability distribution, $\Psi(E)$ can be determined from $\Psi(R, L)$. After defining an eccentricity matrix $E(R_i, L_j)=L_j/(2R_i)$, the probability of each element from the corresponding joint distribution matrix can be appropriately assigned.

III. Exemplary Methods

A. Experimental Parameters

The current framework requires d-PFG experiments performed in both the z-axis and the x-y and x-z planes aligned with the principal axes of the capped cylinders, as discussed in the Theory section and as illustrated in FIGS. 1A-1D. In this case, it is easier to describe the gradient wave vectors within a spherical coordinate system, as defined in FIG. 1A. Each gradient vector is defined by its amplitude; azimuthal angle, $\phi$; and polar angle, $\theta$.

For the purpose of this study, the different experimental parameter sets, $\Omega$, differed only by three parameters, $\Delta$, G, and the relevant angle ($\phi$, $\theta$, and $\tau$ in the case of the x-y plane, x-z plane, and z direction, respectively). This methodology creates a 3-D parameter space for diffusion encoding. The remaining experimental parameters, namely, $\delta=3$ ms and $t_m=0$, were fixed. In addition, the diffusion coefficient was set to be $D=1.8$ $\mu m^2/ms$. Since the wave vector $q=(2\pi)^{-1}\gamma\delta G$ (where $\gamma$ is the gyromagnetic ratio of the labeled spins) reflects the diffusion weighting and provides direct insight to the physical dimensions of the pore, we will use it instead of G.

Although infinite number of possible experimental sets, $\Omega$, exist, a judicious choice of specific experimental parameters improves the size distribution reconstruction. In the present study, we have followed a version of a previously suggested optimization framework. This iterative method is designed to select experimental data sets that balance the need to lower the inherent ill-posedness and increase the MR signal intensity. It is suggested that no single metric of the transfer matrix (e.g., column rank) can be used to predict the quality of the estimation. Instead, the stability of the inversion is related to the transfer matrix column rank, condition number, and signal-to-noise ratio (SNR). In the present work, the selection of the optimal experimental sets was done in two iterative steps. First, an experimental parameter set that results in a full-rank transfer matrix is determined; then this set is used as an initial guess while a search is carried out to find the experimental set that minimizes the transfer matrix's condition number. A detailed description of the algorithm is provided elsewhere.

The dimensions of the capped cylinders were assumed to lie within the range of axonal tissue. In this case, the nominal size in the parallel axis of the cylinder is expected to be larger than that in the perpendicular axis, therefore directly affecting the signal attenuation profiles and leading to generally stronger attenuation in the z-direction. This discrepancy requires the application of weaker gradients in the z and x-z direction experiments. For the estimation of the marginal distributions, we have found that about ten times the number of data than free parameters are needed, which is consistent with previous publications.

1. x-y plane

In the x-y plane the d-PFG method is performed with the direction of $|q_1|=q$ and $(\phi, \theta)=(0, \pi/2)$, while the direction of $|q_2|=q$ was varied in the x-y plane, such that $(\phi, \theta)=(0-\pi, \pi/2)$. (FIG. 1B).

Figure 3:
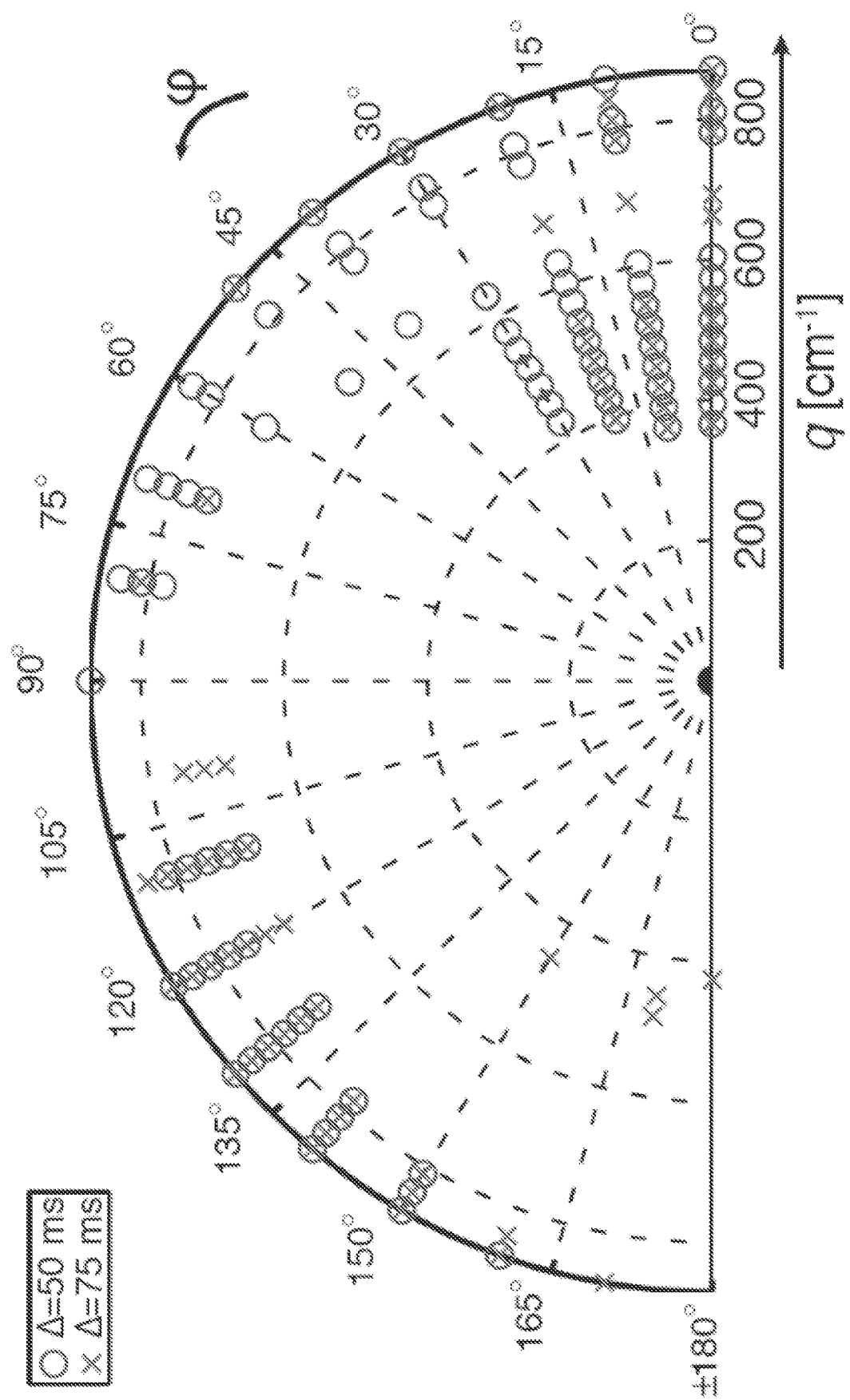
FIG. 3 shows an optimized x-y plane acquisition scheme that includes 160 data sets from the 3-D parametric space spanned by q, $\phi$, and $\Delta$.

The transfer matrix, $E^{xy}(\Omega, R)$, was generated with a cylinder radius range of $0.6$ $\mu m \leq R \leq 10$ $\mu m$ with $0.6$ $\mu m$ steps; this range led to 16 different pore radii. Upon optimization, 160 different experimental sets were chosen from the 3-D parameter space created by $\phi=0-\pi$, $q=366-871$ $cm^{-1}$, and $\Delta=50, 75$ ms. As an example, the optimized experimental sets used in the x-y plane d-PFG are shown in FIG. 3.

2. z Direction

In the z direction d-PFG experiment, the direction of both $|q_1|=q$ and $|q_2|=q\cos(\tau)$ was $(\phi, \theta)=(0, 0)$, while $q_2$ was varied according to $\tau$.

The transfer matrix, $E^{zz}(\Omega, L)$, was generated with a cylinder length range of 5 μm≤L≤40 μm, with 1.4 μm steps; this range led to 26 different pore lengths. Upon optimization, 240 different experimental sets were chosen from the 3-D parameter space created by $\tau=0-\pi$, $q=60-594$ cm$^{-1}$, and $\Delta=50, 75$ ms.

3. x-z Plane

Two versions were used in the x-z plane d-PFG method: (1) the direction of $|q_1|=q$ was $(\phi, \theta)=(0, 0)$, while the direction of $|q_2|=q$ was varied in the x-z plane, such that $(\phi, \theta)=(0, 0-\pi)$; (2) the direction of $|q_1|=q$ was $(\phi, \theta)=(0, \pi/2)$, while the direction of $|q_2|=q$ was varied in the x-z plane, such that $(\phi, \theta)=(0, \pi/2-3\pi/2)$.

The transfer matrix, $E^{xz}(\Omega, R, L)$, was generated with the same R and L steps used to generate $E^{xy}(\Omega, R)$, and $E^{zz}(\Omega, L)$, respectively, which led to 416 different L) combinations. Upon optimization, 150 different experimental sets were chosen from the 3-D parameter space created by $\theta=0-3\pi/2$, $q=59-623$ cm$^{-1}$, and $\Delta=50, 75$ ms.

The typical diffusion length, $L_D=\sqrt{2D\Delta}=16.4$ μm, is shorter than the maximal considered length (40 μm). The mean squared displacement of freely diffusing molecules, $L_D$ should not be used as the maximal restricting dimension, since this assumption implicitly suggests that for a compartment with $L>L_D$, all molecules experience Gaussian diffusion. However, while the mean squared displacement of the ensemble of spins is known, the spins are uniformly distributed within the compartment, and so, often, are their initial positions. When the first diffusion gradient is applied, spins that are close to the compartment boundary do experience restriction, and they are responsible for the deviation from Gaussian diffusion even when $L\gg L_D$. A simulation that demonstrates this deviation is provided here.

Figure 9:
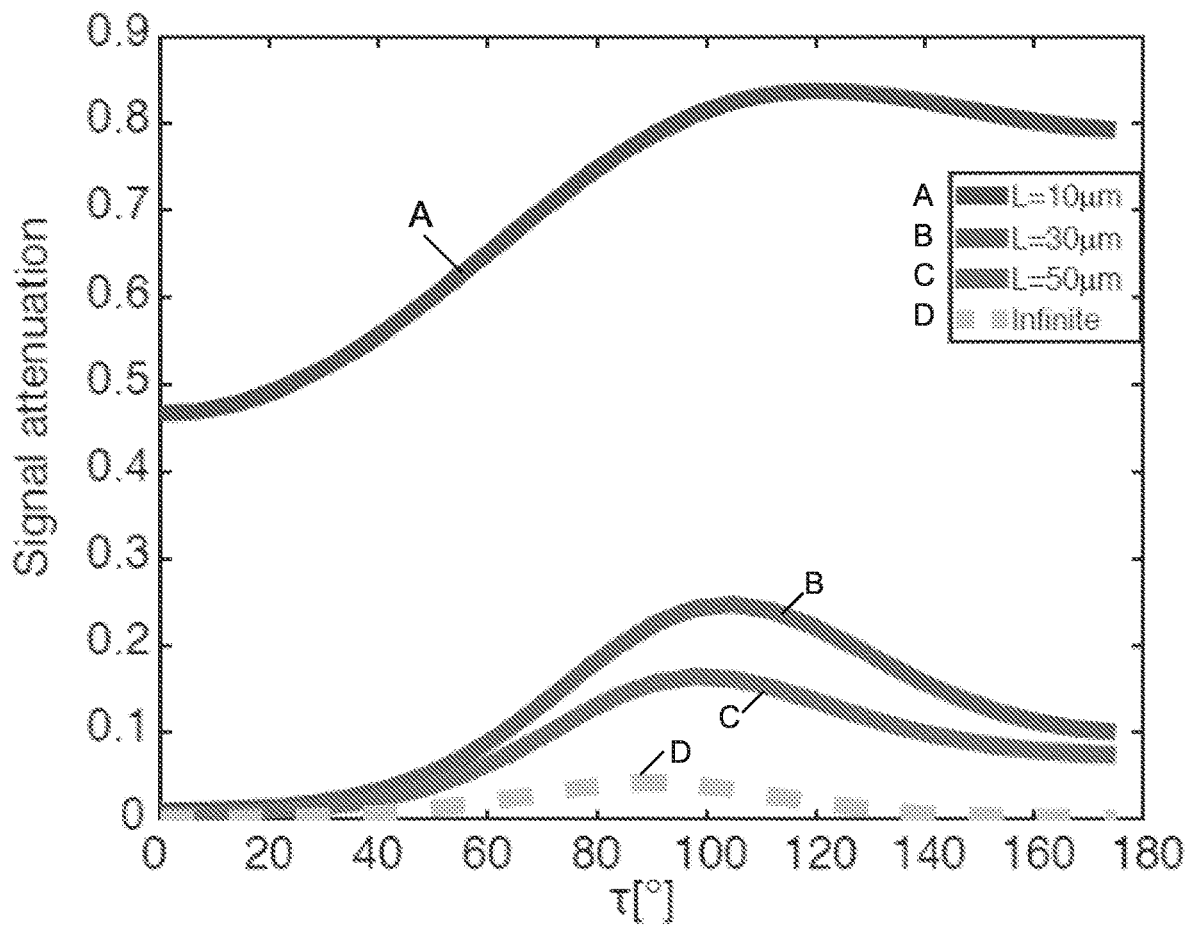
FIG. 9 shows signal attenuation from capped (solid lines) and infinite cylinders (dashed line). Three different lengths of finite cylinders are presented, where all but one subject to $L > L_D$.

It is important to discuss the validity of the selected range of radii and lengths used herein (0.6 μm–10 μm and 5 μm–40 μm, respectively). The relevant experimental parameters, namely, $\Delta_{min}=50$ ms and $D=1.8$ μm$^2$/ms, determine the largest mean squared displacement of water molecules, according to $L_D=\sqrt{2D\Delta}=16.4$ μm. It was previously suggested to use the product of the Einstein diffusion formula as the maximal restricted dimension. This assumption implicitly suggests that for any larger dimension, water molecules experience Gaussian (i.e., free) diffusion. In our case, if one makes this assumption, the upper bound of the possible cylinder radii and lengths has to be 16.4 μm or lower. The MCF signal calculation framework, which is capable of handling arbitrary experimental parameters, can be used to check the validity of such an upper bound. A d-PFG z direction experiment using the current study's experimental parameters and $q=300$ cm$^{-1}$ was simulated, both with capped and infinite cylinder geometries. In the capped cylinder case, three representative lengths were chosen, while all but one were subject to $L>L_D$. It is clear from the simulation results (FIG. 9) that even though the length of the cylinder considerably and even excessively violates $L_D$, the signal attenuation curves do not resemble one that results from freely diffusing spins in the cylinder's parallel axis. It is therefore incorrect to assume Gaussian diffusion along the restricted direction. It is clear that the use of $L_{max}=40$ μm in this case is valid.

4. Inversion Details

All implementations of this theoretical and analysis pipeline were performed with Matlab® (R2013a, The Mathworks, Natick, Mass.) using numerical algorithms. To form the transfer matrix, all of the signal attenuation curves were generated with the multiple correlation function (MCF) method, which was later extended to describe d-PFG MR experiments. The capped cylinder geometry considered in this article is envisioned as a combination of two parallel plates and a cylinder whose symmetry axis is oriented along the z-direction (FIGS. 1A-1D), as previously proposed. The partial volumetric fraction vector, $\Psi$, was then obtained by implementing a non-negative least-square algorithm with an added constraint, that $\Sigma_i \Psi_i=1$ (and for the joint distribution, the additional equality constraint in Eq. 14), using the lsqlin Matlab function. Note that no regularization was used in the fitting process. For the moment, we avoid using regularization methods since they are problem specific, and the selection of the regularization parameter may affect the results.

Because of the equality constraints, the reconstruction of the joint distribution was possible with fewer equations than unknown variables, namely, 150 and 416, respectively. The stability of this underdetermined system results in a relatively low number of required MR acquisitions and thus a feasible experimental design.

Throughout the study the estimation quality was assessed based on the Jensen difference between the theoretical and estimated PSDs. The Jensen difference metric is a symmetric version of the Kullback-Leibler divergence, and always yields a finite value. The difference between two PSDs, Q and P, is defined as $$d_{JD} = \sum_i \left[ \frac{P_i \ln(P_i) + Q_i \ln(Q_i)}{2} - \left(\frac{P_i + Q_i}{2}\right) \ln\left(\frac{P_i + Q_i}{2}\right) \right]. \quad (15)$$

The Jensen difference metric was chosen since it is a well-established method of measuring the similarity between two probability distributions.

B. Simulated Joint Distribution Phantoms

Figure 4A:
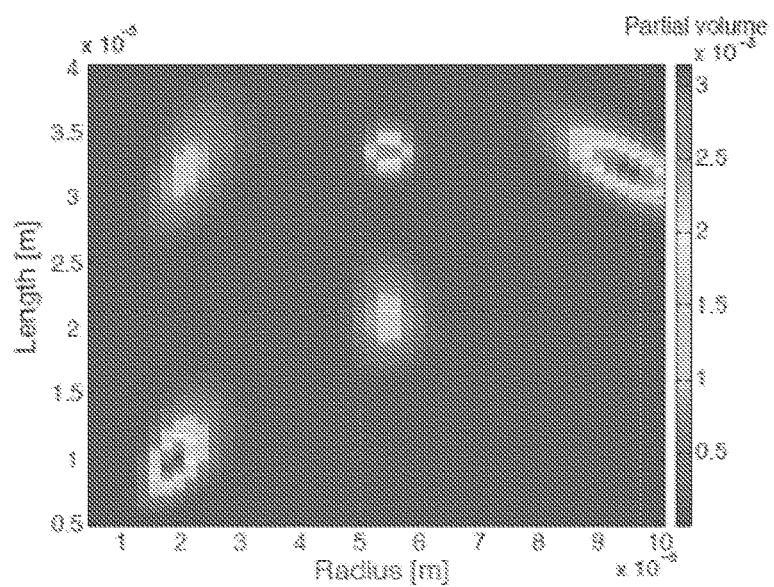
FIGS. 4A-4C show exemplary joint R-L distribution phantoms representing two realistic cases of microstructure: (4A) five narrow peaks (referred to as "dense-narrow") and (4B) three broad peaks (referred to as "scattered-broad") in the R-L space, while in (4C), a more general and demanding distribution is considered (referred to as "random-diagonal").
Figure 4B:
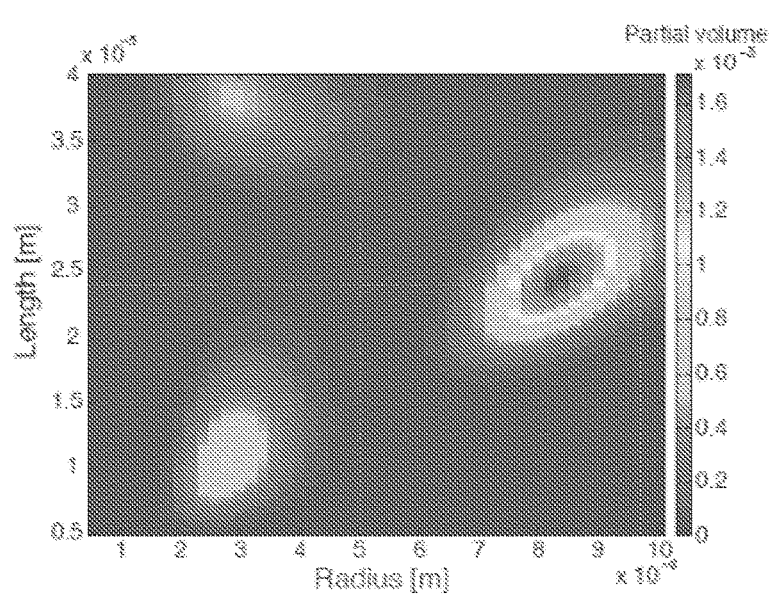
Figure 4C:
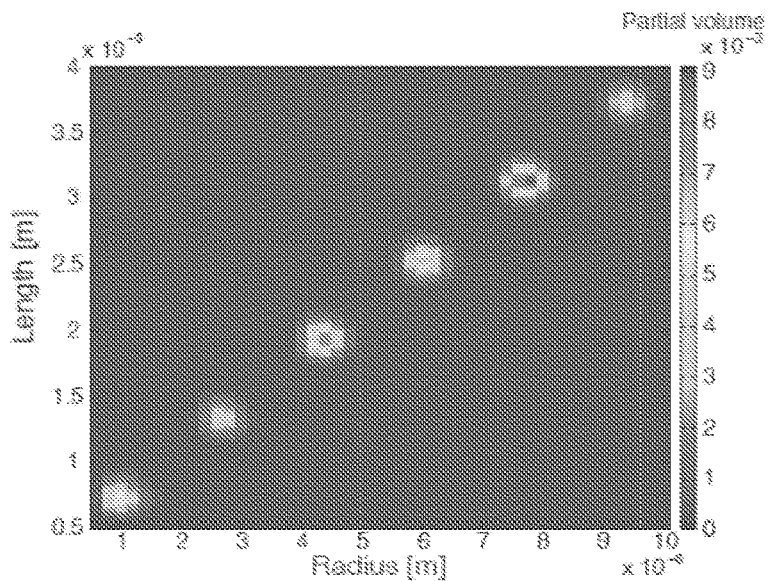

In the case of axon bundles, one often sees pore size distributions that appear to be lognormal or multimodal, as in many distributions occurring in nature and granular media. This notion had led us to use a weighted linear combination of bivariate lognormal distribution functions to form two joint R-L distribution phantoms (FIGS. 4A and 4B). In addition, to demonstrate the power of the presented approach, a more general R-L distribution was considered (FIG. 4C). While this distribution is clearly not realistic, its marginal radius and length distributions have very few non-negative coefficients, thus making the estimation process more challenging.

The general form of the log normal probability density function we used was $$f(R, L) = \frac{1}{2\pi R L \tilde{\sigma}_R \tilde{\sigma}_L \sqrt{1-\rho^2}} \left( \exp\left[ -\frac{1}{2(1-\rho^2)} \times \left[ \left(\frac{\log(R) - \tilde{R}_0}{\tilde{\sigma}_R}\right)^2 - 2\rho \left(\frac{\log(R) - \tilde{R}_0}{\tilde{\sigma}_R}\right) \times \left(\frac{\log(L) - \tilde{L}_0}{\tilde{\sigma}_L}\right) + \left(\frac{\log(L) - \tilde{L}_0}{\tilde{\sigma}_L}\right)^2 \right] \right] \right), \quad (16)$$

-continued where $$\tilde{\sigma}_x = \left[\log\left(1 + \frac{\sigma_x^2}{x_0^2}\right)\right]^{\frac{1}{2}}$$

$$\tilde{x}_0 = \log(x_0) - \left(\frac{\tilde{\sigma}_x^2}{2}\right).$$

$x_0$ and $\sigma_x$ are the mean and standard deviation of either R or L, and $\rho$ is the correlation coefficient of log(R) and log(L).

The following three joint R-L distribution phantoms were generated and simulated:
1. Dense-narrow peak distribution: Five bivariate log normal probability density functions, as shown in FIG. 4A, with the following parameters: centers (all in μm) $(R_0, L_0)$=(2.0, 10.4), (2.2, 32.4), (9.5, 32.2), (5.5, 21.0), (5.5, 33.5); standard deviations (all in μm) $(\sigma_R, \sigma_L)$= (0.25, 1.5), (0.30, 2.0), (0.40, 1.1), (0.30, 2.0), (0.20, 1.0); correlation coefficients ρ=(0.5, 0.5, −0.7, 0, 0); and relative fractions 0.25, 0.15, 0.25, 0.2, 0.15.
2. Scattered-broad peak distribution: Three broad bivariate log normal probability density functions, as shown in FIG. 4B, with the following parameters: centers (all in μm) $(R_0, L_0)$=(3.0, 12.0), (3.2, 38.4), (8.5, 25.2); standard deviations (all in μm) $(\sigma_R, \sigma_L)$=(0.50, 3.0), (0.80, 3.0), (0.65, 2.5); correlation coefficients ρ=(0.35, −0.25, 0.55); and relative fractions 0.25, 0.25, 0.50.
3. Random-diagonal peak distribution: Six narrow bivariate log normal probability density functions, as shown in FIG. 4C, with the following parameters: centers (all in μm) $(R_0, L_0)$=(1.0, 7.4), (2.7, 13.4), (4.4, 19.4), (6.0, 25.4), (7.7, 31.4), (9.4, 37.4); all with the same standard deviations (in μm), $(\sigma_R, \sigma_L)$=(0.20, 0.8) and correlation coefficients, ρ=0; the relative fractions were randomly generated and were 0.15, 0.11, 0.21, 0.17, 0.25, 0.11.

To approach the continuous nature of an actual size distribution, the signal attenuation profile, $E^{data}(\Omega)$, was generated using an appropriate transfer matrix with very fine, equal-sized spatial steps of 0.2 μm in both R and L. In addition, all of the generated signal curves were corrupted by Gaussian white noise. For each distribution, two noise standard deviations were analyzed, namely, 0.5% and 1% relative to the signal attenuation without any diffusion gradient applied.

IV. Results

The joint R-L distribution of capped cylinders was estimated after following the steps described schematically in FIG. 2. Three joint distributions were simulated (FIGS. 4A-4C), ac-counting for different peak widths and separations.

A. Advantage of Constraints

To provide clear evidence that using the marginal radius and length distributions as equality constraints in the joint distribution estimation can improve the results, the estimation of the joint distribution was performed without using the marginal distributions, though they may be used in other methods. Furthermore, some comparisons may include in the estimation process all of the data points from the x-y plane, and the direction, along with the x-z plane acquisition originally proposed to estimate the joint distribution.

By including the underlying data sets of the marginal distributions, the transfer matrix can be over determined (e.g., all 160, 240, and 150 experimental sets from the x-y plane, z direction, and x-z plane, respectively).

In one example, the dense-narrow peak distribution phantom with noise standard deviation of 0.5% was used for the comparison. This particular phantom may represent the "easiest" case for estimation, because of the relatively small number of non-zero elements, and the low noise level, though other phantoms may be used.

Figure 5:
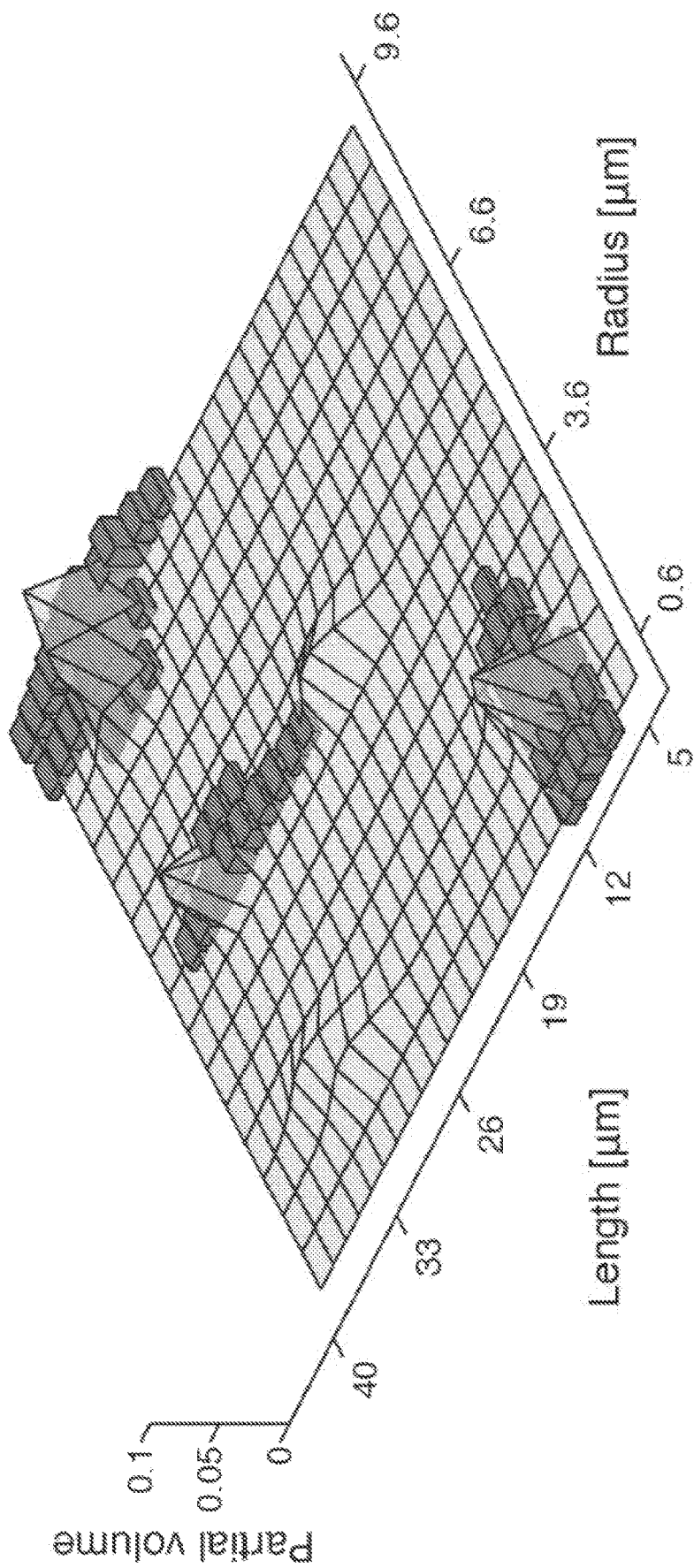
FIG. 5 shows a theoretical (solid surface) and estimated (bins) joint R-L distribution of a dense-narrow peak distribution phantom with a noise standard deviation of 0.5%, without the use of the equality constraints.
Figures 6A, 6B, 6C:
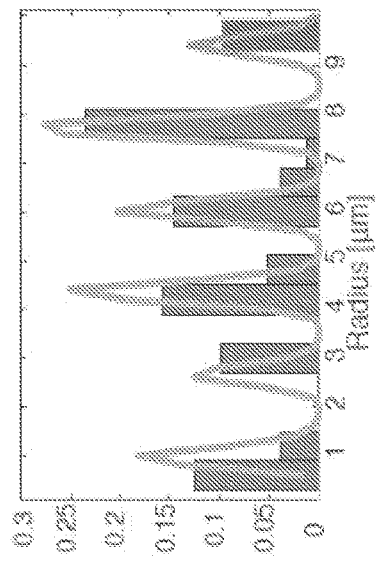
Figures 6D, 6E, 6F:
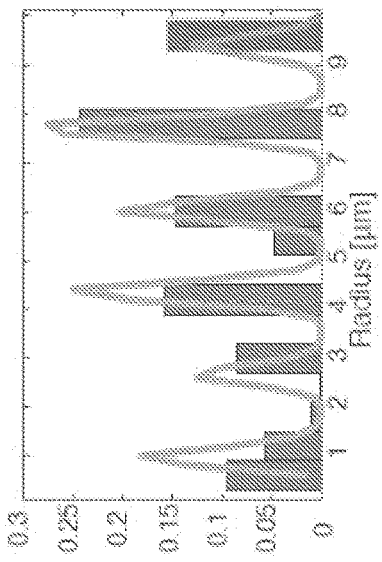
Figure 8A:
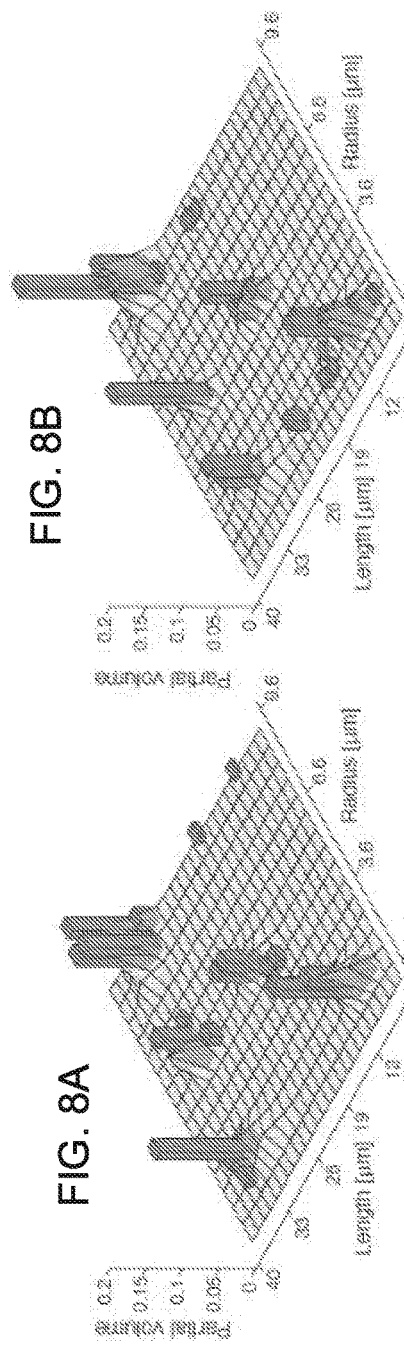
FIGS. 8A-8F show the theoretical (solid surface) and estimated (bins) joint R-L distributions of all of the phantoms. Dense-narrow distribution with noise standard deviations of (8A) 0.5% and (8B) 1%. Scattered-broad distribution with noise standard deviations of (8C) 0.5% and (8D) 1%. Random-diagonal distribution with noise standard deviations of (8E) 0.5% and (8F) 1%.
Figure 8B:
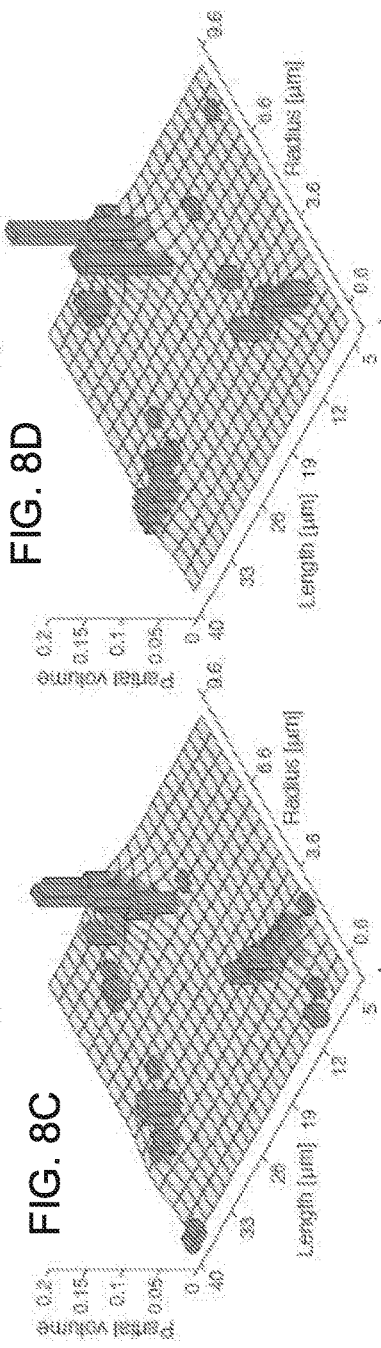
Figure 8C:
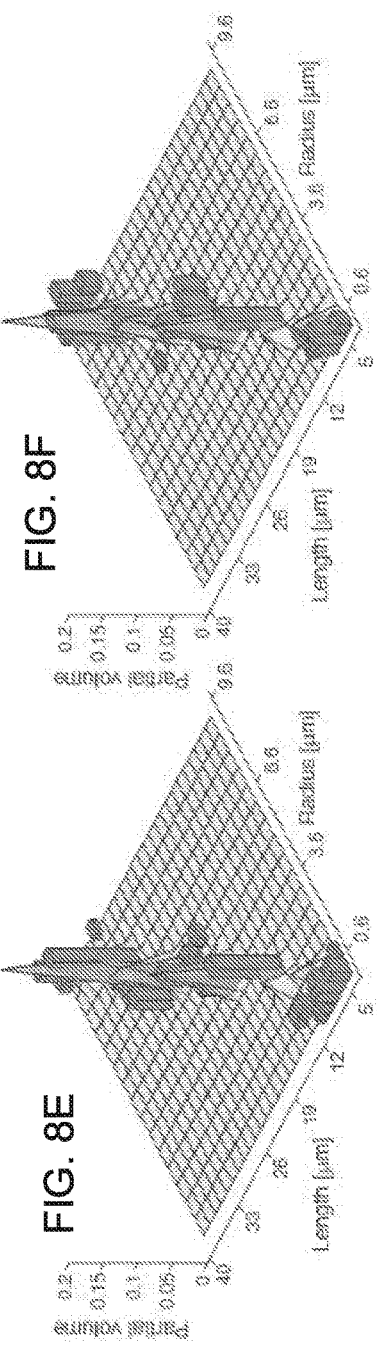
Figure 8D:
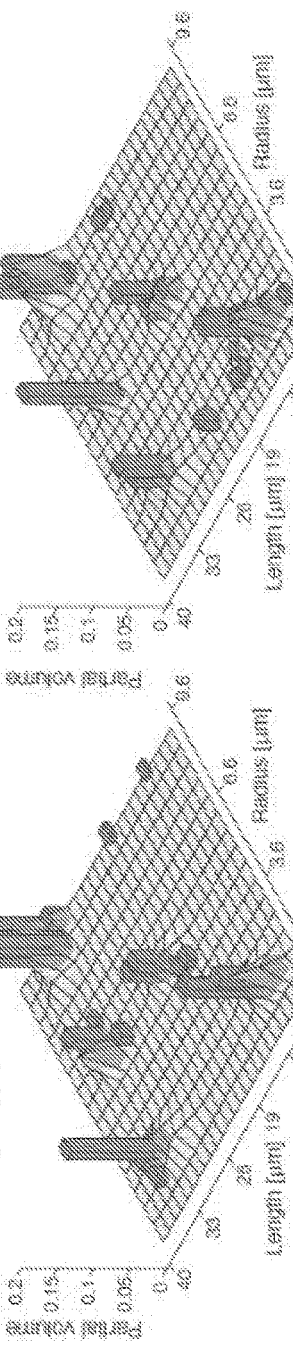

In FIG. 5, the theoretical joint distribution (solid surface) and the estimated joint distribution (bins) are shown after solving the minimization problem in Eq. 3 without the equality constraints. FIG. 5 can be compared to FIG. 8A.

B. Marginal and Joint Distributions Estimations

As described herein, the MRD can be estimated using an x-y plane d-PFG method. In FIGS. 6A-6F, the theoretical MRDs of all of the phantoms are shown as a function of the radius (solid line), while the estimated MRDs are overlaid on it (bins). Given the narrow peak distribution (FIG. 4A), its MRDs are presented in FIGS. 6A and 6D, which correspond to noise standard deviations of 0.5% and 1%, with a Jensen differences of 0.0393 and 0.0431, respectively. The MRDs of the broad peak distribution in FIG. 4B, are presented in FIGS. 6B and 6E, which correspond to noise standard deviations of 0.5% and 1%, with a Jensen differences of 0.0653 and 0.1032, respectively. Lastly, the MRDs of the random-diagonal peak distribution in FIG. 4C, are presented in FIGS. 6C and 6F, which correspond to noise standard deviations of 0.5% and 1%, with Jensen differences of 0.0764 and 0.0867, respectively.

The MLD can be estimated from a z-direction d-PFG method. In FIGS. 7A-7F, the theoretical MLDs of all of the phantoms are shown as a function of the radius (solid line), while the estimated MLDs are overlaid on it (bins). The MLDs of the narrow peak distribution (FIG. 4A) are presented in FIGS. 7A and 7D, which correspond to noise standard deviations of 0.5% and 1%, with a Jensen differences of 0.0524 and 0.0807, respectively. The MLDs of the broad peak distribution in FIG. 4B, are presented in FIGS. 7B and 7E, which correspond to noise standard deviations of 0.5% and 1%, with a Jensen differences of 0.0480 and 0.1185, respectively. Lastly, the MLDs of the random-diagonal peak distribution in FIG. 4C, presented in FIGS. 7C and 7F, correspond to noise standard deviations of 0.5% and 1%, with Jensen differences of 0.1131 and 0.1197, respectively.

Figure 8E:
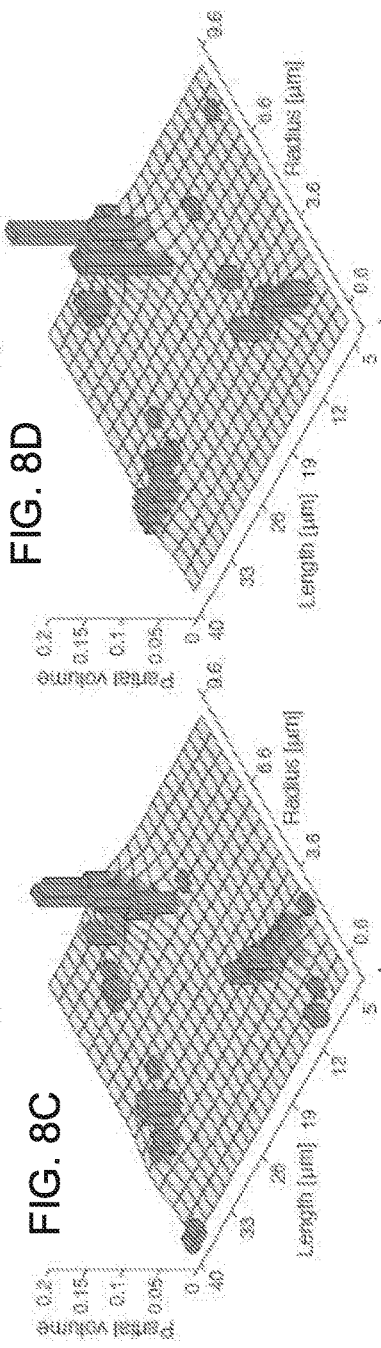
Figure 8F:
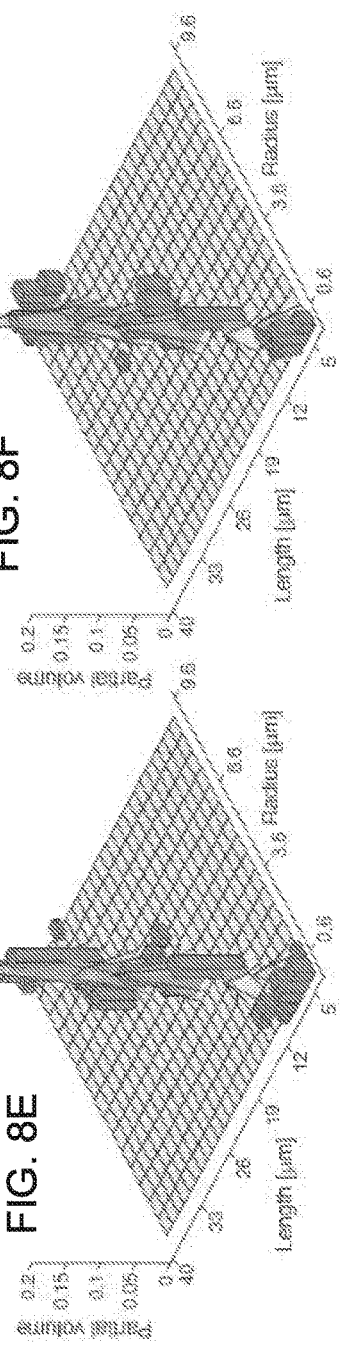

Unless the radii and lengths of the ensemble of cylinders are statistically independent, the marginal distributions provide only a fraction of the microstructural information. To obtain the full description from the joint R-L distribution, an x-z plane d-PFG method can be used. In FIGS. 8A-8D, the theoretical (solid surface) joint distributions of all of the phantoms and the estimated ones (bins) are shown. The narrow peak R-L distributions are presented in FIGS. 8A and 83, which correspond to noise standard deviations of 0.5% and 1%, with Jensen differences of 0.2703 and 0.2774, respectively. The broad peak distributions are presented in FIGS. 8C and 8D, which correspond to noise standard deviations of 0.5% and 1%, with Jensen differences of 0.3407 and 0.3464, respectively. Lastly, the random-diagonal peak distributions are presented in FIGS. 8E and 8F, which correspond to noise standard deviations of 0.5% and 1%, with a Jensen differences of 0.2343 and 0.2184, respectively.

The influence of added noise can be seen by following the changes in the Jensen differences. For the MRDs, an SNR decrease resulted in a Jensen difference increase by 10%, 58%, and 13%, for the narrow, broad, and diagonal peak distributions, respectively. For the MLDs, an SNR decrease resulted in a Jensen difference increase by 54%, 147%, and 6%, for the narrow, broad, and diagonal peak distributions, respectively. Interestingly, for the joint distributions, SNR decreases resulted in Jensen difference increases by only 2.6% and 1.7% for the narrow and broad distributions, respectively, and a 6.8% decrease for the diagonal peak distribution.

V. Discussion

Disclosed are exemplary methods for estimating the non-parametric joint radius-length distribution of an ensemble of capped cylinders. Some disclosed methods include the innovative use the use of 3-D d-PFG MR acquisition to obtain marginal radius and length distributions. In some methods, the marginal radius and length distributions are employed as equality constraints in the estimation of the joint R-L distribution. Disclosed methods exploit the ability to acquire the MR signal from orthogonal cross-sections of the pore by selectively applying the diffusion gradients along different directions.

Some 3-D d-PFG methods can include three steps. First, the direction of the diffusion gradients is kept in the x-y plane, allowing estimation of the MRD by treating the capped cylinder as an infinite cylinder. Second, the d-PFG gradient pairs are applied along the z-axis, so that the MLD is estimated by treating the capped cylinders as parallel plates. The third step includes applying gradients in the x-z plane, which results in MR signal attenuation that is influenced by the distribution of both pore length and radius. Although there may be many coefficients to estimate in the joint R-L distribution, a relatively small number of acquisitions can be used to reconstruct it. The transfer matrix that is used to obtain the joint distribution can be underdetermined, due to the use of the previously estimated MRD and MRL as equality constraints.

In one example, three joint R-L distribution phantoms, exhibiting a range of pore morphologies, were used to demonstrate the versatility of the described methods. The first two cases represented realistic scenarios for axonal morphology, and contained joint distributions with five narrow peaks (referred to as "dense-narrow") and three broad peaks (referred to as "scattered-broad") in the R-L parameter space. The third phantom (referred to as "random-diagonal') contained a more general R-L distribution to establish the power of the disclosed methods. In all cases, the MRDs, MLDs, and joint R-L distributions were estimated subject to different noise (SNR) levels ($\sigma$=0.005, 0.01).

To show that using the marginal radius and length distributions as equality constraints in the joint distribution estimation indeed improves the results, estimation without constraints was performed. The dense-narrow distribution with $\sigma$=0.005 case was used as a phantom because of the relatively small number of non-zero elements, and the low noise level. This step was done with excluding the marginal distributions as equality constraints but including all 160, 240, and 150 experimental sets from the x-y plane, z-direction, and x-z plane, respectively. The resulting joint distribution reconstruction is clearly inaccurate, as two out of the five peaks are missing, and the rest of the estimated peaks are much broader than theory (FIG. 5).

In contrast, when using the equality constraints, the reconstruction of the dense-narrow peaks proved fairly stable to noise level increases for both the marginal and joint distributions. This stability can be seen qualitatively from FIGS. 6A-6F, 7A-7F, and 8A-8F, and quantitatively from the minor changes in the Jensen difference (a 10%, 54%, and 2.6% change for the MRD, MLD, and joint, respectively) due to decreases in the SNR.

With the exception of the joint distribution estimation, the reconstructions of the scattered-broad peak distributions were sensitive to decreasing SNR, for both marginal distributions. Generally, as the size distribution becomes broader, including a greater number of non-zero values, reconstruction of the peak distribution becomes less stable. Therefore, large standard deviations that result in wider peaks along with low SNR can yield estimates with lower accuracy. Even though the Jensen difference increased by 58% and 147% for the MRD and MLD respectively, it only increased by 1.7% for the joint distribution.

The random-diagonal phantom provided a test case in which both of the marginal distributions always have more non-zero than zero elements, with a random variable amplitude. This case also proved fairly stable to noise level increases, as can be seen from the minor changes in the Jensen difference (a 13%, 6%, and 6.8% change for the MRD, MLD, and joint, respectively) due to decreases in the SNR.

One advantage of using the marginal distributions as equality constraints is that it reduces the effective number of unknown parameters in the joint distribution. It may therefore be important to look at the number of non-negative elements found while estimating the marginal distributions, since they may later determine the remaining unknown parameters in the joint distribution estimation process. For the exemplary dense-narrow peaks, the marginal distributions reveal that there are about 8 and about 13 non-negative radii and lengths, respectively. With these as equality constraints, the number of remaining unknowns for the joint distribution is 104, effectively making the system over determined (the x-z method had 150 data sets). This may is not the case for the other distributions, where the remaining unknowns are 276 (scattered-broad) and 230 (random-diagonal), making the system underdetermined. The robustness to noise level and standard deviation of the joint R-L distribution are remarkable since the estimation is performed with what is potentially a very underdetermined system (416 partial volume elements), which its uncertainty is reduced by the constraints.

The ranges of radii and lengths within the joint distribution phantoms are based on beaded axonal morphologies, and the expected ranges of these values such a specimen may contain. Little information regarding the shape of the joint distribution of beaded axons was previously available; therefore one currently lacks a priori information to impose for assuming a particular parametric size or shape distribution. Furthermore, severity of the injury may affect the form of the joint R-L distribution; therefore, assuming a specific parametric distribution is usually not warranted. The estimated marginal and joint distributions described herein are nonparametric, and, therefore, not based on any assumed pore size or eccentricity.

A judicious choice of specific experimental parameters, and/or increased dimensionality of the parametric space (by varying other new salient parameters, e.g., $\delta$) can improve the stability of the size distribution estimation. In the disclosed methods, a d-PFG 3-D parameter space of independent experimental variables can be assumed, from which the values of q, $\phi/\theta/\tau$, and $\Delta$ can be selected according to an optimization scheme described herein. Exemplary optimized data point sets from an x-y plane d-PFG method are shown in FIG. 3. Other experimental design optimization schema can be incorporated into the joint radius-length distribution estimation framework, as an additional preliminary step.

Described d-PFG methods can be uniquely suited to pore size and shape characterization. The ability to perform the d-PFG methods in a chosen physical plane enables the estimation of the joint radius-length distribution. In addition, the advantages of the d-PFG methods over s-PFG methods in the context of the pore size distribution estimation problem have been shown and discussed, and experimentally demonstrated. The application of two PFG pairs (i.e., d-PFG) as opposed to one (i.e., s-PFG) results in a higher sensitivity to different pore sizes, making the solution to this inverse problem less ill-posed. Moreover, use of the d-PFG experiment leads to more and new information, increasing the dimensionality of the column space of the transfer matrix, making the estimation more robust.

For use in the context of neural tissue, specifically white matter, disclosed methods may be applied with an assumption that axons are coherently oriented finite cylinders. In the case of brain white matter tissue, fascicles containing axons may take on all possible orientations within an imaging volume. Two general cases of cylinder orientation may occur, namely, parallel cylinders of unknown direction, or cylinders subject to a general orientation distribution function (ODF). To identify the case, a preliminary diffusion tensor imaging (DTI) scan can be used. The amount of anisotropy resulting from a DTI method can be related to the orientational coherence within a voxel, as cylinders with a broad ODF may appear to be more isotropic. After identifying and establishing the suitable orientation description, we provide two experimental and analytical strategies to address the problem.

If the cylinders are found to be parallel with a varying orientation over different voxels, an adjustment to the experimental design is necessary. A 3-D gradient sampling scheme can be used that that involves the application of the current circular d-PFG acquisition in different orientations, similar to the design of DTI experiments. The principal fiber orientation in each voxel can then be calculated from a subset of these measurements (or from the previous DTI scan), and the projection of the data onto the desired plane can be used and analyzed. This strategy is especially well-suited for the joint distribution estimation framework, since a 3-D d-PFG acquisition can be used.

If the cylinders are found to be randomly oriented, one can use the current experimental framework and only address the orientation distribution with a slight analytical addition. A uniform orientation distribution (i.e., random orientation) of cylinders can be assumed, thus modifying the calculation of the signal attenuation constructing the transfer matrix. The isotropic nature of the macrostructure may eliminate the possibly of decoupling R and L, and obtaining the marginal distributions. A more complicated orientation distribution (i.e., not random) requires additional free parameters.

The determination of the joint radius-length distribution permits direct quantification of CSA. This framework was introduced using the capped cylinder geometry, but can be implemented for any anisotropic pore shape that is solvable with the multiple correlation function (MCF) method (e.g., ellipsoids with different major and minor axes). Measuring the CSA of injured (beaded) axons may help to characterize and quantify the amount of damage to the tissue and shed light on the injury mechanism and the possible microstructural changes that may occur following the injury. To adapt the model to real nervous tissue, additional components can be added to the current capped cylinders, such as a distribution of infinite cylinders, representing healthy axons, and a Gaussian or non-Gaussian extracellular diffusion compartment. Such a model may provide vital information about changes following injury, or even during development, The disclosed technology can have many different applications, including the exemplary use in the context of axon injury. For example, diffusion weighed MR techniques can be used to determine skeletal muscle architecture. The length and cross-sectional area of myocytes are structural features that are proportional to muscle force and velocity that can be directly obtained from a joint radius-length distribution. Following changes in the joint distribution can help to understand the way that muscle tissue responds to freezing and thawing alternations in food sciences applications or help understand and improve tissue preservation in transplantation applications. Furthermore, the disclosed technology may also be used to directly measure noninvasively the CSA of sieve tube elements, thus shedding light on nutrient translocation within plants, or in assessing freezing and thawing of vegetables.

The disclosed methods and general approaches may be used to solve other types of inverse problems, such as inverting 2D and higher-dimensional Fredholm equations of the first kind, such is described in U.S. Provisional Patent Application No. 62/000,316, which was filed on May 19, 2014 and is incorporated by reference herein in its entirety. For example, the disclosed methods can be used to reconstruct two-dimensional Inverse Laplace Transform (2D-ILT) data from 1D projections and their application as linear constraints. In this way, 2D-ILT can be reconstructed using fewer data more robustly using the disclosed methods. Furthermore, the disclosed methods can be used for reconstructing MR images using 2D and 3D k-space data and for reconstructing average propagators in each voxel of an MRI image from diffusion weighted MRI data, which is described further in U.S. Pat. No. 7,711,171, entitled "Estimation of the Average Propagator from Magnetic Resonance Data," which is incorporated by reference herein in its entirety. The estimation of the joint distribution from a set of marginal distributions using the herein disclosed algorithms and methods can be applied generally to a much larger class of inverse problems that arise in many areas of physical sciences, imaging sciences, and data analysis.

VI. Signal Acquisition

Figure 10:
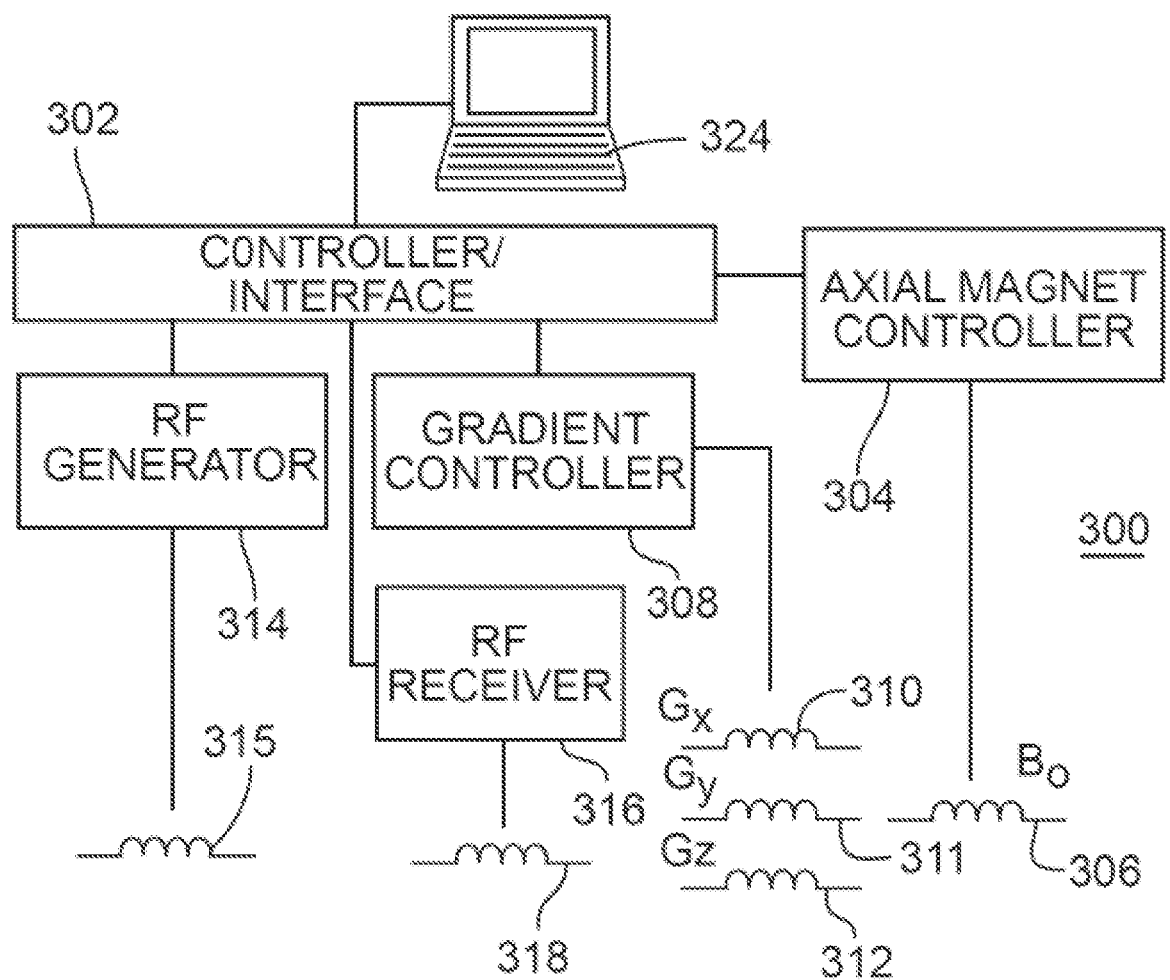
FIG. 10 is schematic illustration of an exemplary magnetic resonance (MR) apparatus.

MR signals as described herein can be obtained using an exemplary MRI apparatus 300 as illustrated in FIG. 10. The apparatus 300 includes a controller/interface 302 that can be configured to apply selected magnetic fields such as constant or pulsed fields to a target (e.g., a patient or specimen). An axial magnet controller 304 is in communication with an axial magnet 306 that is generally configured to produce a substantially constant magnetic field Bo. A gradient controller 308 is configured to apply a constant or time-varying gradient magnetic field in a selected direction or in a set of directions using magnet coils 310-312 to produce respective magnetic field gradients $G_x$, $G_y$, $G_z$ or combinations thereof. An RF generator 314 is configured to deliver one or more RF pulses to a target using a transmitter coil 315. An RE receiver 316 is in communication with a receiver coil 318 and is configured to detect or measure net magnetization of spins. Slice selection gradients can be applied with the same hardware used to apply the diffusion gradients.

The gradient controller 308 can be configured to produce pulses or other gradient fields along one or more axes. By selection of such gradients as described in, for example, U.S. Pat. No. 5,539,310, an effective diffusion tensor can be found. In addition, the gradient controller 308 can be configured to apply gradient pulses or other gradient magnetic fields of different magnitudes, and associated MR signals can be detected by the RF receiver 316. A computer 324 or other processing system such as a personal computer, a workstation, a mobile computing device, or a networked computer can be provided for data acquisition, control and/or analysis. The computer 324 may include a hard disk, a removable storage medium such as a floppy disk or CD-ROM, and/or other memory such as random access memory (RAM). Computer-executable instructions for data acquisition or control can be provided on any form of tangible data storage media, and/or delivered to the computer 324 via a local area network, the Internet, or other network. Signal acquisition, instrument control, and signal analysis can be performed with distributed processing. For example, signal acquisition and signal analysis or processing can be performed at different locations.

MR signals can be obtained for a variety of q-vectors, i.e., q-values and q-directions. Signals can be obtained by fixing a magnitude and duration of an applied pulsed-gradient magnetic field or effective magnitude of other spin-encoding magnetic field (i.e., fixing q), and varying the direction in which the encoding field is applied. After signals associated with the various directions are obtained, the q is changed and another series of signals at the various directions is obtained. Alternatively, signals can be obtained by fixing the direction of the applied encoding field and varying q. The direction of the encoding field can then be changed, and signals as a function of q can be obtained.

Other signal acquisition sequences can also be used. For example, while double PFG NMR and MRI acquisition are described in this application, in particular, other forms of multiple PFG NMR and MRI experiments can be used. In addition, diffusion encoding can occur prior to the MRI acquisition as a "filter" or it can be embedded or incorporated within the imaging sequence itself.

Figure 11:
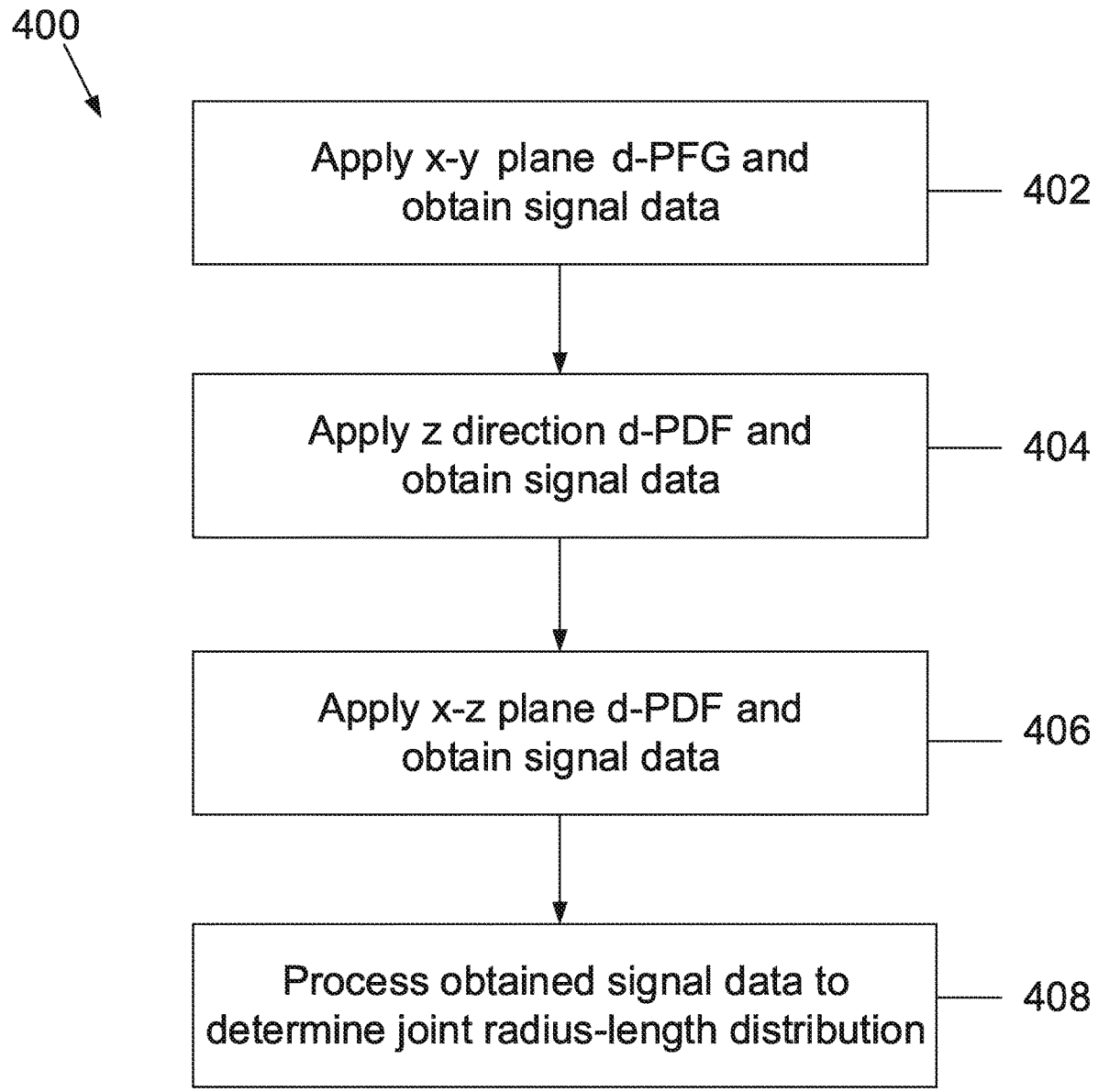
FIG. 11 is a flow chart illustrating an exemplary method of collecting MR data.

A representative method 400 is illustrated in FIG. 11. In a step 402, an MR apparatus, such as illustrated in FIG. 10, can be used to apply x-y plane d-PFG to a target and to obtain corresponding signal data in response. For example, for application of the x-y plane d-PFG, the direction of $|q1|=q$ can be set to $(\phi, \theta)=(0, \pi/2)$, while the direction of $|q2|=q$ is varied in the x-y plane, such that $(\phi, \theta)=(0-\pi, \pi/2)$. In a step 404, the MR apparatus can be used to apply z direction d-PFG to the target and to obtain corresponding signal data in response. For example, for application of the z direction d-PFG, the direction of both $|q1|=q$ and $|q2|=q \cos(\tau)$ can be $(\phi, \theta)=(0, 0)$, while q2 is varied according to τ. In a step 406, the MR apparatus can be used to apply x-z plane d-PFG to the target and to obtain corresponding signal data in response. For example, for application of the x-z plane d-PFG, the direction of $|q1|=q$ can be $(\phi, \theta)=(0, 0)$, while the direction of $|q2|=q$ is varied in the x-z plane, such that $(\phi, \theta)=(0, 0-\pi)$; or the direction of $|q1|=q$ can be $(\phi, \theta)=(0, \pi/2)$, while the direction of $|q2|=q$ is varied in the x-z plane, such that $(\phi, \theta)=(0, \pi/2-3\pi/2)$. Other signal acquisition sequences can be used. At 408, the signal data obtained in steps 402, 404, and 406 are processed as described herein to determine a joint radius-length distribution of the target.

The method 400 of FIG. 11 shows steps performed in a specific order, but these steps can be performed in different orders, and model parameters for restricted and hindered signal components can be estimated in a common step or in a series of steps, which is further described in U.S. Pat. Nos. 7,643,863 and 8,380,280, which are incorporated by reference herein in their entirety. Different models can be selected for other specimens, and the cylindrical model described herein is only a representative example.

VII. Additional Features and Applications

The disclosed technology can provide a means to reveal the three-dimensional changes in axon morphology following injury (e.g., beading) via the two-dimensional size distribution (e.g., diameters and lengths of axons). By implementing this framework, the nonparametric eccentricity distribution of ex-vivo sciatic nerves were estimated in an injury model, providing a noninvasive quantification of rat sciatic nerves axonal beading.

In exemplary methods, rat sciatic nerves were excised and subjected to axial tension sufficient to induce beading or minimal tension to straighten their macroscopic undulation (control). These nerves were immediately immersed in fixative and rehydrated in phosphate buffered saline (PBS) prior to acquiring MR data. The MR acquisition protocol disclosed herein was used on the injury model tissue. The acquired signals were processed accordingly and resulted in 2D radius-length distributions of several specimens.

Figure 12:
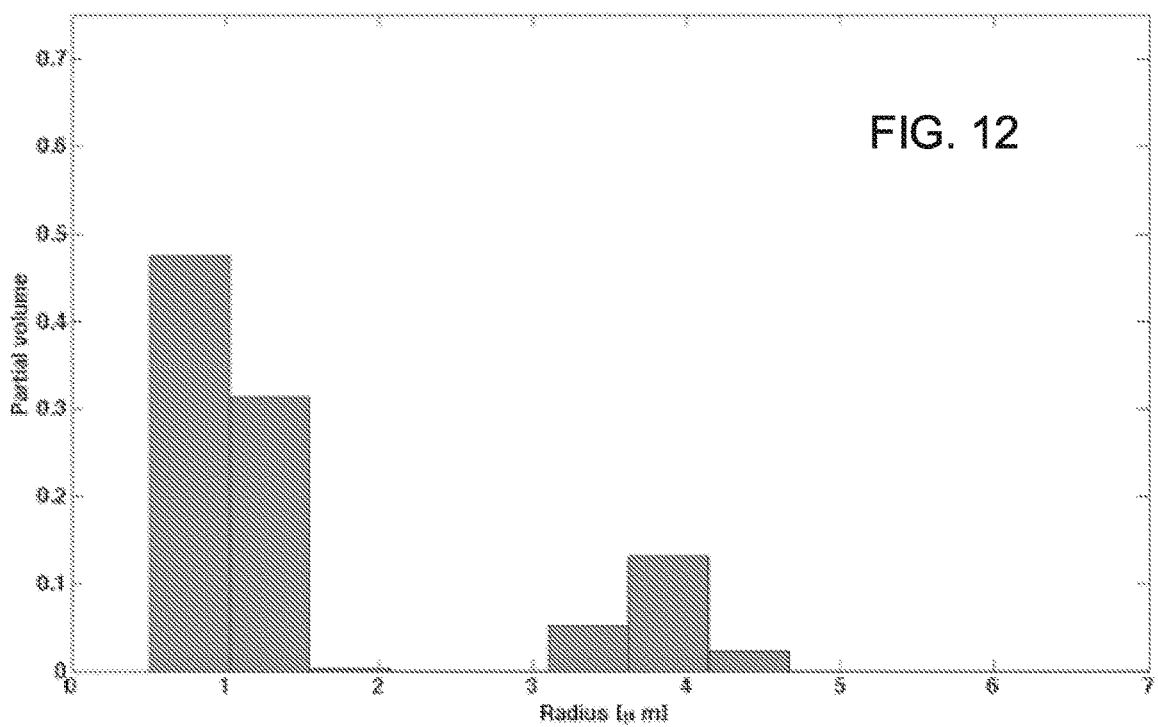
FIG. 12 illustrates an exemplary marginal radius distribution (MRD) for injured rat sciatic nerves.
Figure 13:
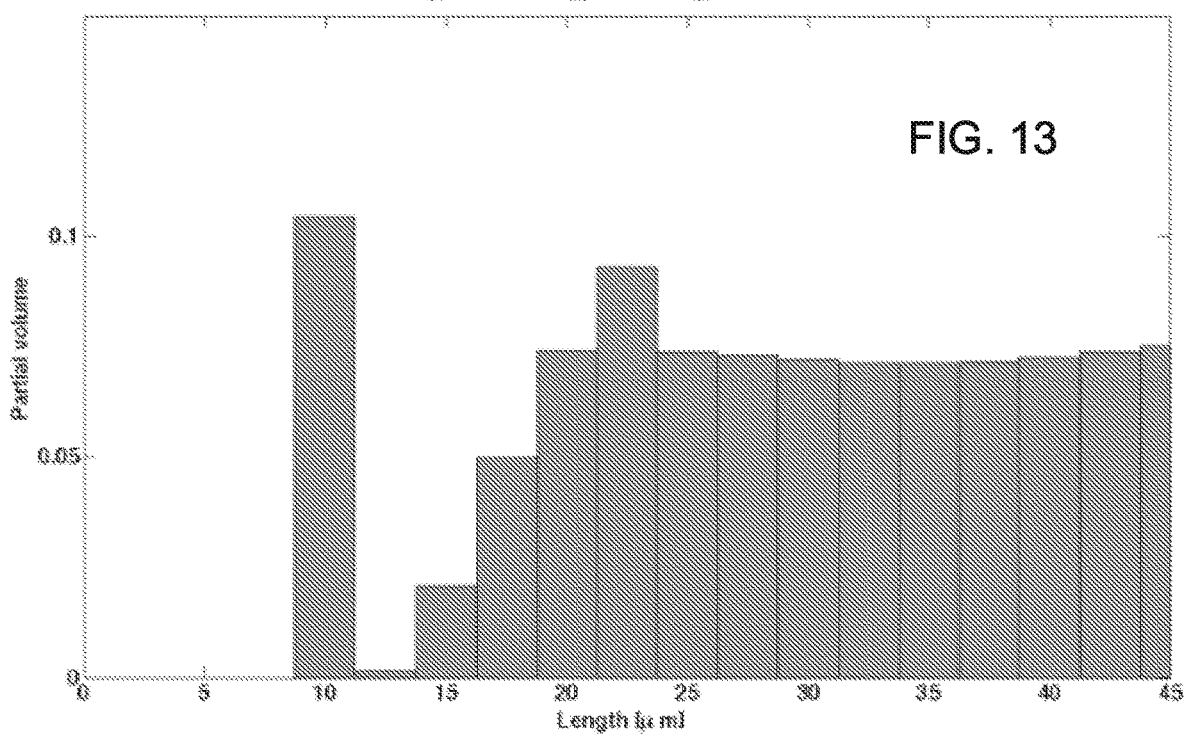
FIG. 13 illustrates an exemplary marginal length distribution (MRD) for injured rat sciatic nerves.
Figure 14:
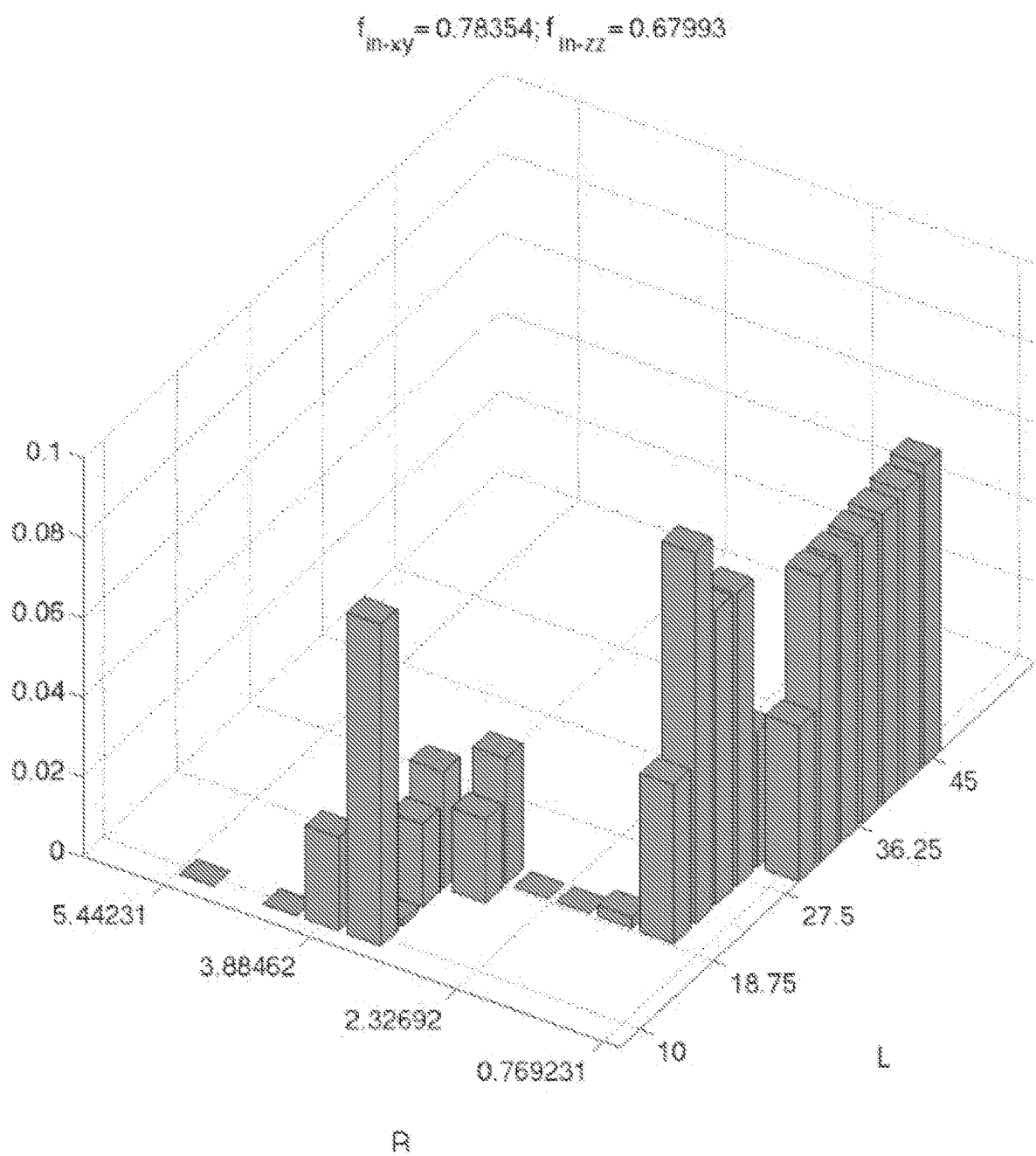
FIG. 14 illustrates a joint 2D radius-length distribution derived from the data shown in FIGS. 12 and 13.

Results from applying the disclosed methods on rat sciatic nerve injury model are illustrated in FIGS. 12-14. The marginal radius distribution (MRD) and marginal length distribution (MLD) are shown in FIG. 12 and FIG. 13, respectively. These marginal distributions are then used to derive the joint 2D R-L distribution, which is illustrated in FIG. 14. Note the two distinct groups evident from the joint 2D distribution, wide and short axons, and narrow and long axons. This partitioning illustrates the microstructural changes resulting from axonal beading, The disclosed technology can be utilized for quantification of axonal injury following mild traumatic brain injury (mTBI) and TBI. This technology can reveal microstructural changes resulting from injury that currently no other noninvasive method offers. By focusing on axons that are beaded and characterizing their morphological features, a key feature of brain trauma can be isolated and focused upon with high specificity.

A series of ex vivo experiments on rat sciatic nerve injury models have been performed, along with validation via microscopy. In addition, this technology can be applied with normal patients and patients who have sustained mild TBI to detect beading in vivo. For example, the disclosed MRI sequences can be adapted to run on clinical scanners so that this technology can be used with normal human subjects and human patients with mTBI (and other non-human subjects/patients as well).

The disclosed technology can be used for the noninvasive quantification of axonal beading. In addition, the disclosed technology can be used in other fields. For example, 2D MR diffusion/relaxation spectroscopy (e.g., $T_1$-$T_2$, $T_2$-D, D-D, $T_2$-$T_2$) methods are currently rarely used in vivo due to long acquisition times. However, the disclosed technology can be used with 2D MR diffusion and/or relaxation spectroscopy to greatly reduce the acquisition time by stabilizing the 2D spectrum reconstruction in a similar manner to that disclosed herein for 2D R-L distributions. Applying the disclosed methods in this scenario can enable the acquisition of this data orders of magnitude more rapidly than is currently possible without the disclosed technology, making these informative 2D-spectroscopic approaches suitable for biological and clinical implementation.

The disclosed technology for the analysis of pore size and shape has applicability beyond the analysis of beading of axons and neuritis. For example the disclosed technology can also be used in the field of porous media nuclear magnetic resonance (NMR), such as to analyze pore morphology in rocks and other earth formations (e.g., for oil exploration and water aquifer assessment). The disclosed technology can also be used in the food industry for analyzing the effects of storing produce and freezing of meat. The disclosed technology can specifically be used to study muscle myocytes in meat. In particular, The disclosed technology can be used for assessing food quality, texture and structure via NMR under different conditions of food preservation.

For purposes of this description, certain aspects, advantages, and novel features of the embodiments of this disclosure are described herein. The disclosed methods and systems should not be construed as limiting in any way. Instead, the present disclosure is directed toward all novel and nonobvious features and aspects of the various disclosed embodiments, alone and in various combinations and subcombinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the specification and attached figures may not show all the various ways in which the disclosed methods can be used in conjunction with other methods.

The singular terms "a", "an", and "the" include plural referents unless context clearly indicates otherwise. The term "comprises" means "includes without limitation." The term "coupled" means physically linked and does not exclude intermediate elements between the coupled elements. The term "and/or" means any one or more of the elements listed. Thus, the term "A and/or B" means "A", "B" or "A and B."

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope of the following claims.

The invention claimed is:

1. A method for estimating a joint radius-length distribution of an ensemble of pores, the method comprising:
    receiving data obtained from three-dimensional (3-D) diffusion-based magnetic resonance (MR) acquisition;
    determining a marginal radius distribution (MRD) and a marginal length distribution (MLD) for an ensemble of pores based on the data obtained from 3-D diffusion-based MR; and
    determining a joint radius-length distribution for the ensemble of pores based on data obtained from 3-D diffusion-based MR and based on the MRD and the MLD;
    wherein the received 3-D diffusion-based MR acquisition data comprises MR data associated with different orthogonal dimensions of the porous elements based on selective application of diffusion gradient vectors with components along different orthogonal dimensions;
    wherein the diffusion gradient vectors comprise:
        a first diffusion gradient applied in a first plane substantially perpendicular to a porous length dimension of the pores;
        a second diffusion gradient applied in a first direction along an axis substantially parallel to the porous length dimension of the pores; and
        a third diffusion gradient applied in a second plane perpendicular to the first plane and parallel to the first direction.

2. The method of claim 1, wherein the joint radius-length distribution is determined based in part on a non-negative least-squared minimization to estimate relative volumetric fractions of pore sizes using the MRD and MLD as constraints.

3. The method of claim 1, wherein the joint radius-length distribution, $\Psi(R, L)$, is constrained so that:

$$\sum_j \Psi(R, L_j) = \Psi(R) \text{ and } \sum_i \Psi(R_i, L) = \Psi(L).$$

4. The method of claim 1, wherein the joint radius-length distribution is a nonparametric joint radius-length distribution.

5. The method of claim 1, wherein 3-D diffusion-based MR data acquisition comprises:
    applying dual pulsed field gradient (d-PFG) MR diffusion gradients in an x-y plane substantially perpendicular to a longitudinal length dimension of the pores to determine the MRD of the pores;
    applying d-PFG MR diffusion gradients in a direction along a z axis substantially parallel to the longitudinal length dimension of the pores to determine the MLD of the pores; and
    applying d-PFG MR diffusion gradients in an x-z plane of the pores to produce an MR signal that is influenced by both the length and the radius of the pores.

6. The method of claim 5, wherein:
    the pores are represented as infinite cylinders when applying d-PFG MR diffusion gradients in the x-y plane;
    the pores are represented as parallel plates when applying d-PFG MR diffusion gradients in a direction along the z axis; and
    the pores are represented by both length and radius when applying d-PFG MR diffusion gradients in the x-z plane.

7. The method of claim 1, wherein estimating the nonparametric joint radius-length distribution comprises using a transfer matrix that is undetermined.

8. The method of claim 1, wherein the pores comprise anisotropic finite-length porous elements.

9. The method of claim 1, wherein estimating the joint radius-length distribution comprises estimating a joint radius-length eccentricity distribution of the anisotropic finite porous elements.

10. The method of claim 1, wherein the pores comprise injured axons.

11. The method of claim 10, wherein the injured axons exhibit local compartment eccentricity variation due to injury.

12. The method of claim 1, wherein the pores comprise myocytes or other muscle tissue elements.

13. The method of claim 1, wherein the pores comprise plant sieve tube elements.

14. The method of claim 1, wherein the pores are modeled as capped cylinders having a finite length.

15. A system comprising:
    a magnetic resonance (MR) system operable to apply three-dimensional (3-D) diffusion-based MR to an ensemble of pores and acquire resulting MR signal data from the applied 3-D diffusion-based MR;

an MR data processing system configured to determine a marginal radius distribution (MRD) and a marginal length distribution (MLD) for the ensemble of pores based on the data obtained from 3-D diffusion-based MR, and configured to determine a joint radius-length distribution for the ensemble of pores based on data obtained from the applied 3-D diffusion-based MR and based on the MRD and the MLD;

wherein the MR system is operable to acquire MR signal data from different orthogonal dimensions of the pores by selectively applying diffusion gradient vectors along different orthogonal dimensions of the pores;

wherein the diffusion gradient vectors comprise:
- a first diffusion gradient applied in a first plane substantially perpendicular to a porous length dimension of the pores;
- a second diffusion gradient applied in a first direction along an axis substantially parallel to the porous length dimension of the pores; and
- a third diffusion gradient applied in a second plane perpendicular to the first plane and parallel to the first direction.

16. A storage device storing computer-executable instructions for causing a computer to perform the method of claim 1.

17. The method of claim 1, wherein receiving data obtained from 3-D diffusion-based MR acquisition comprises receiving data obtained from 3-D dual pulsed field gradient (d-PFG) MR acquisition.

18. The system of claim 15, wherein the 3-D diffusion-based MR comprises 3-D dual pulsed field gradient (d-PFG) MR.

19. The method of claim 1, further comprising utilizing the joint radius-length distribution to quantify axonal injury following traumatic brain injury to reveal microstructural changes resulting from injury.

* * * * *